(12) United States Patent
Shomi

(10) Patent No.: US 8,216,528 B2
(45) Date of Patent: Jul. 10, 2012

(54) SAMPLE PREPARATION KIT, SAMPLE PREPARATION CONTAINER, AND SAMPLE PROCESSING DEVICE

(75) Inventor: Keiichiro Shomi, Kobe (JP)

(73) Assignee: Sysmex Corporation, Hyogo (JP)

( * ) Notice: Subject to any disclaimer, the term of this patent is extended or adjusted under 35 U.S.C. 154(b) by 1356 days.

(21) Appl. No.: 11/525,797

(22) Filed: Sep. 25, 2006

(65) Prior Publication Data

US 2007/0069054 A1 Mar. 29, 2007

(30) Foreign Application Priority Data

Sep. 29, 2005 (JP) ................................. 2005-283183
Sep. 29, 2005 (JP) ................................. 2005-283342

(51) Int. Cl.
*B01L 3/00* (2006.01)
*G01N 1/28* (2006.01)
(52) U.S. Cl. .................... 422/536; 422/527; 422/547
(58) Field of Classification Search .............. 422/61, 422/68.1, 99, 100, 101, 102, 104, 292, 300, 422/939, 536, 527, 547; 436/174, 177, 179, 436/180; 73/53.01, 64.56
See application file for complete search history.

(56) References Cited

U.S. PATENT DOCUMENTS

| | | | |
|---|---|---|---|
| 4,678,559 A * | 7/1987 | Szabados | ........................ 209/17 |
| 4,859,610 A * | 8/1989 | Maggio | ........................ 436/518 |
| 5,282,978 A | 2/1994 | Polk, Jr. et al. | |
| 6,358,474 B1 * | 3/2002 | Dobler et al. | ................... 422/99 |
| 2002/0066812 A1 | 6/2002 | Gazeau | |
| 2003/0092170 A1 | 5/2003 | Pressman et al. | |
| 2006/0078474 A1 | 4/2006 | Yamamoto et al. | |

FOREIGN PATENT DOCUMENTS

| | | |
|---|---|---|
| FR | 2 793 261 | 11/2000 |
| JP | 63-112974 | 5/1988 |
| JP | 63-112974 A | 5/1988 |
| JP | 7-6746 | 1/1995 |
| JP | 2000-333669 A | 12/2000 |
| WO | 2005/085800 A1 | 9/2005 |

* cited by examiner

*Primary Examiner* — Jill Warden
(74) *Attorney, Agent, or Firm* — Sughrue Mion, PLLC

(57) ABSTRACT

A sample preparation kit is described, a representative one of which includes: a tissue container for containing tissue from a living body and comprising a convex part on an inner bottom of the container; and a crushing tool for crushing the tissue contained in the tissue container by using the convex part.

12 Claims, 27 Drawing Sheets

[Fig. 1]
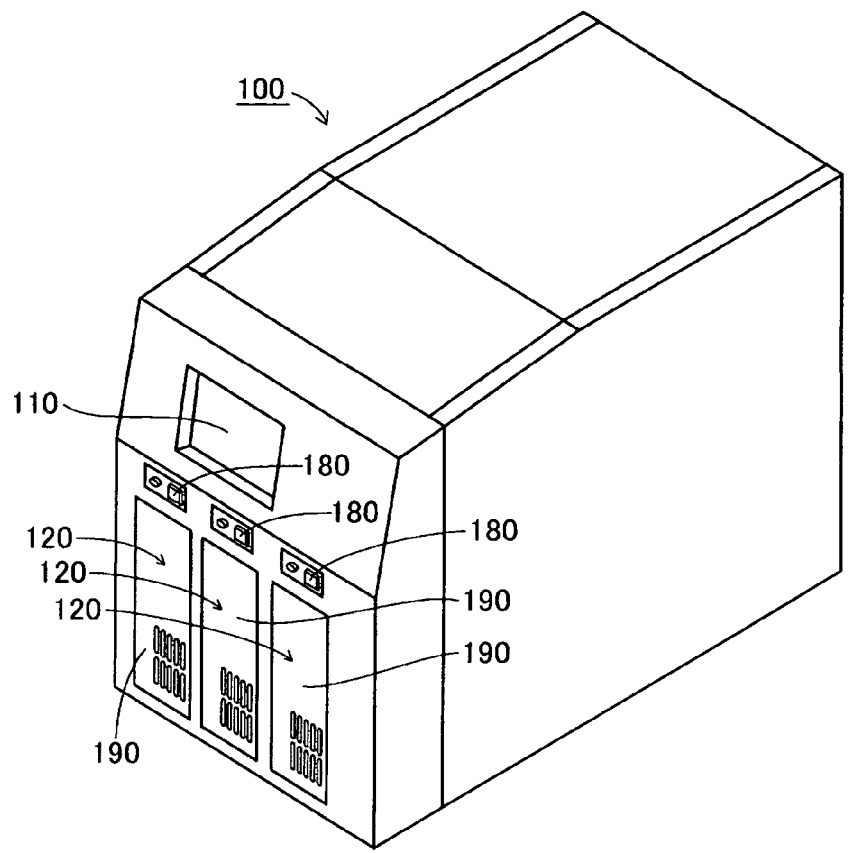
[Fig. 2]
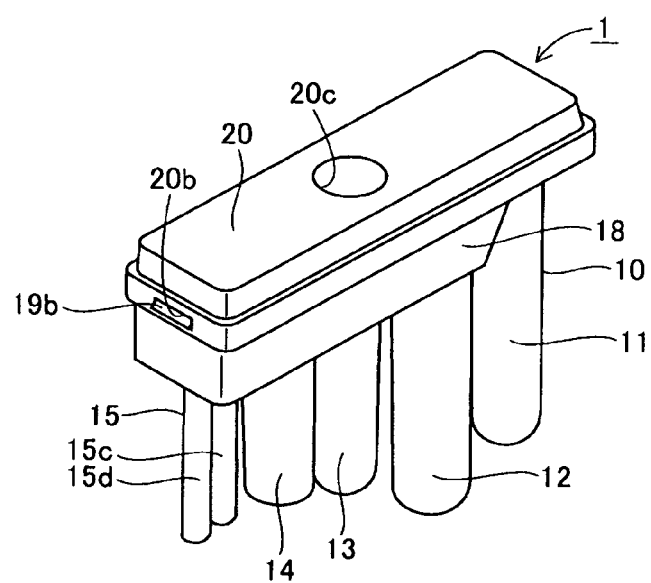

[Fig. 3]
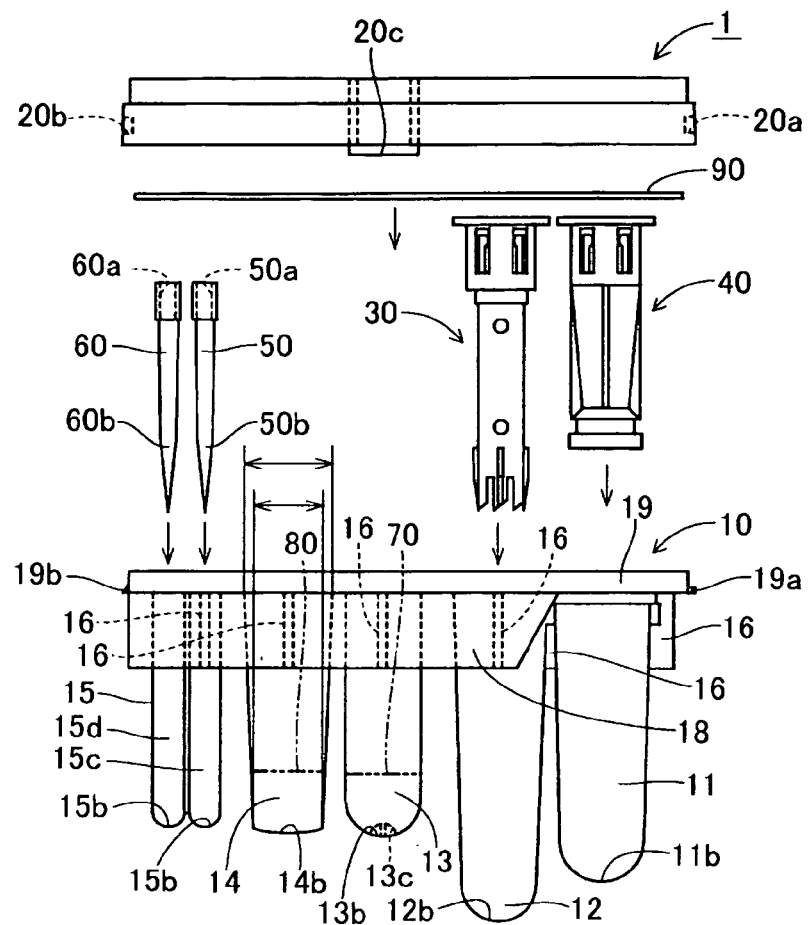
[Fig. 4]
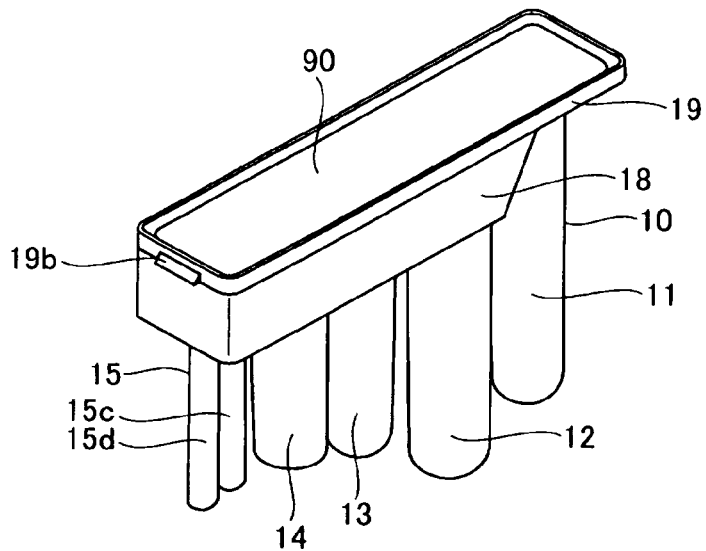

[Fig. 5]
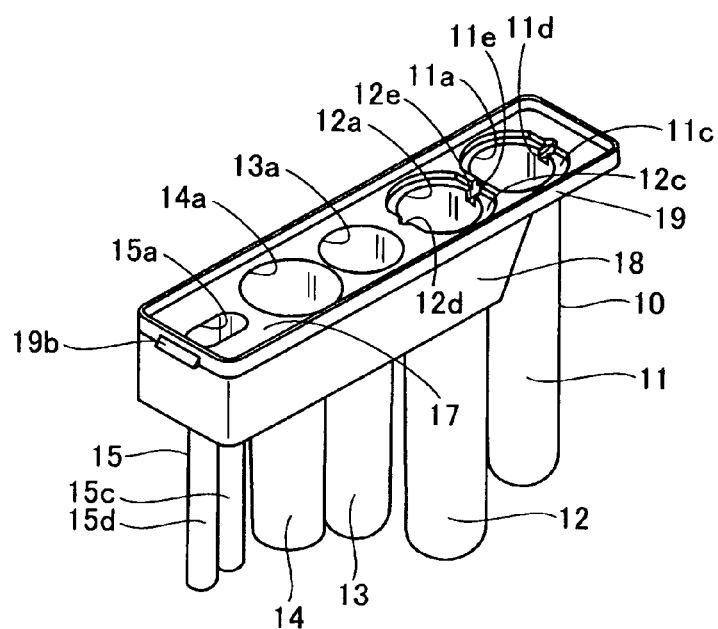
[Fig. 6]
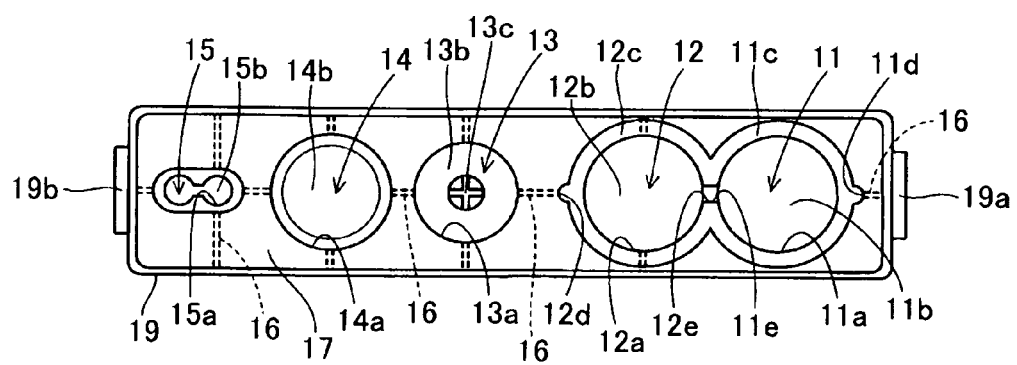

[Fig. 7]
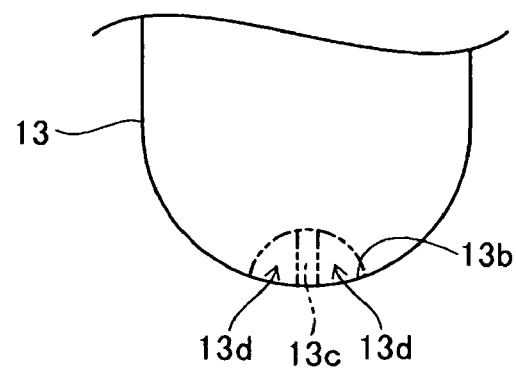
[Fig. 8]
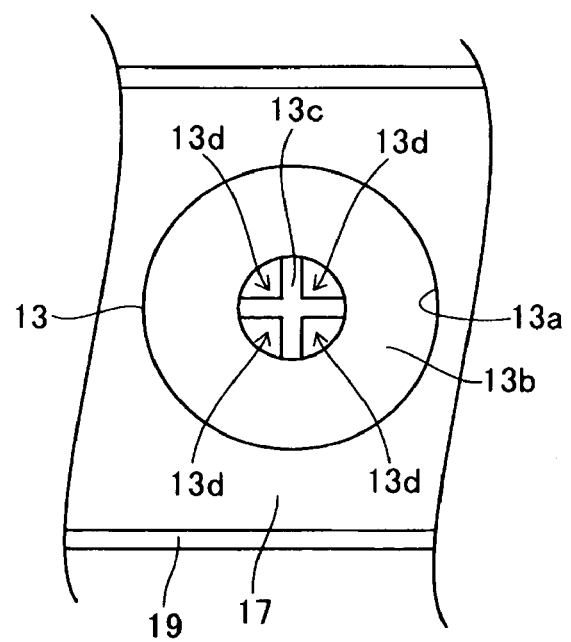

[Fig. 9]
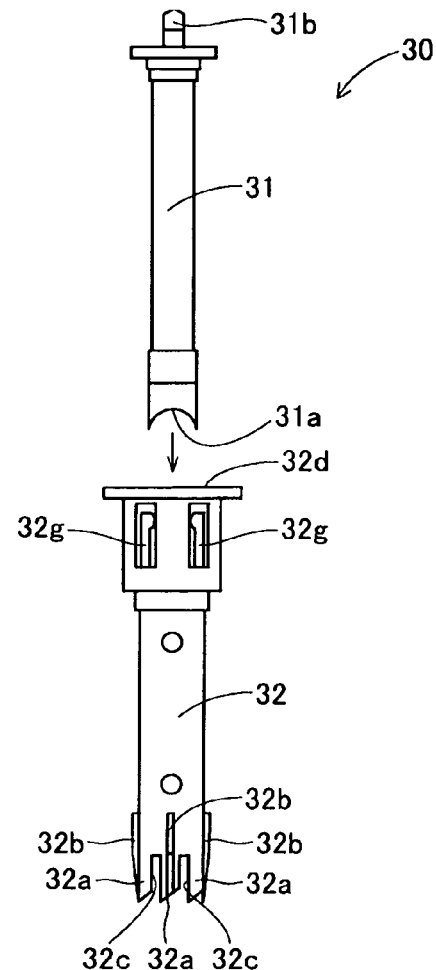
[Fig. 10]
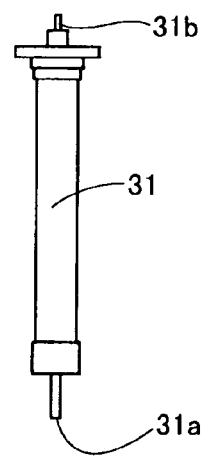

[Fig. 11]
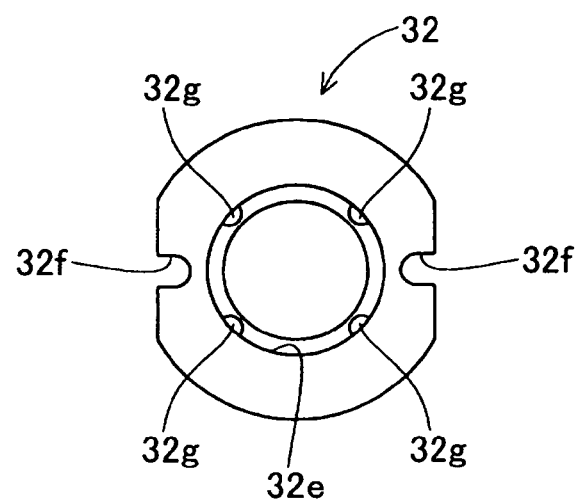
[Fig. 12]
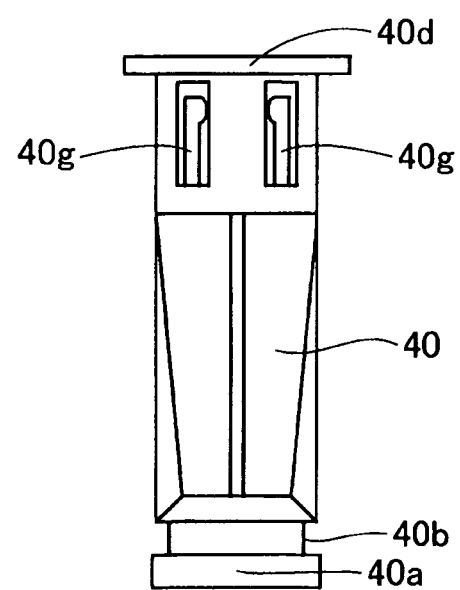

[Fig. 13]
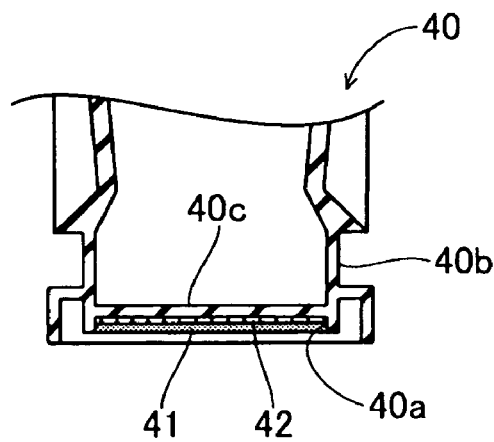
[Fig. 14]
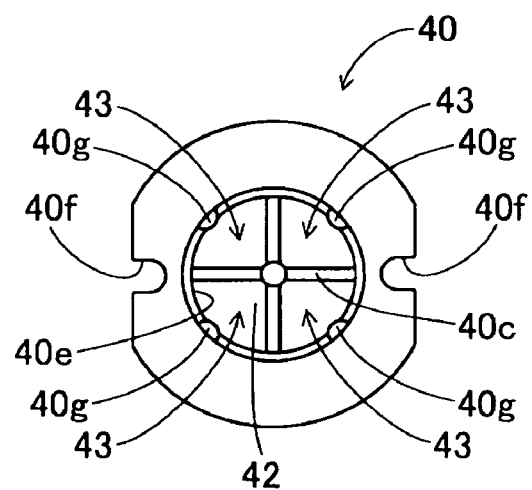

[Fig. 15]
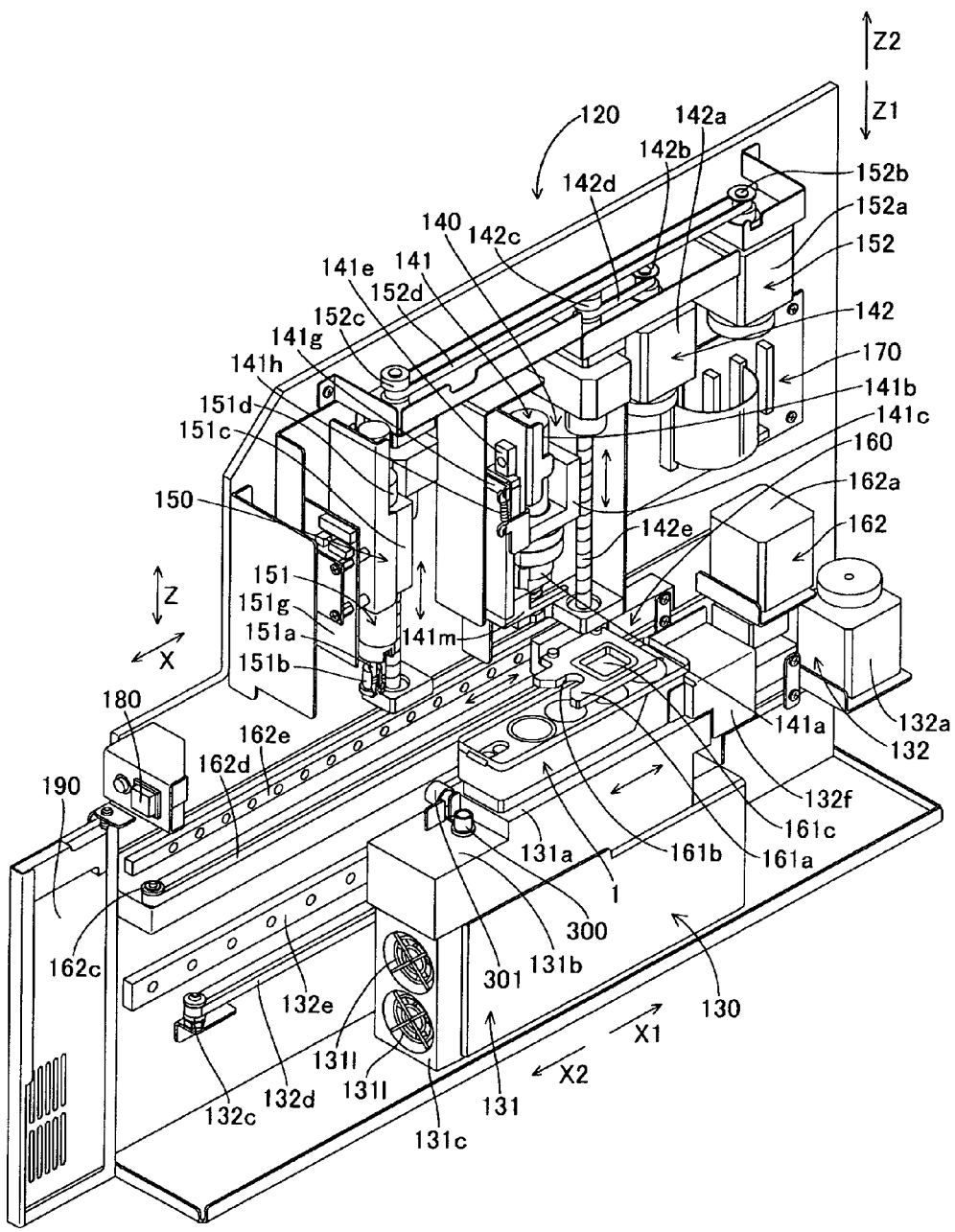

[Fig. 16]
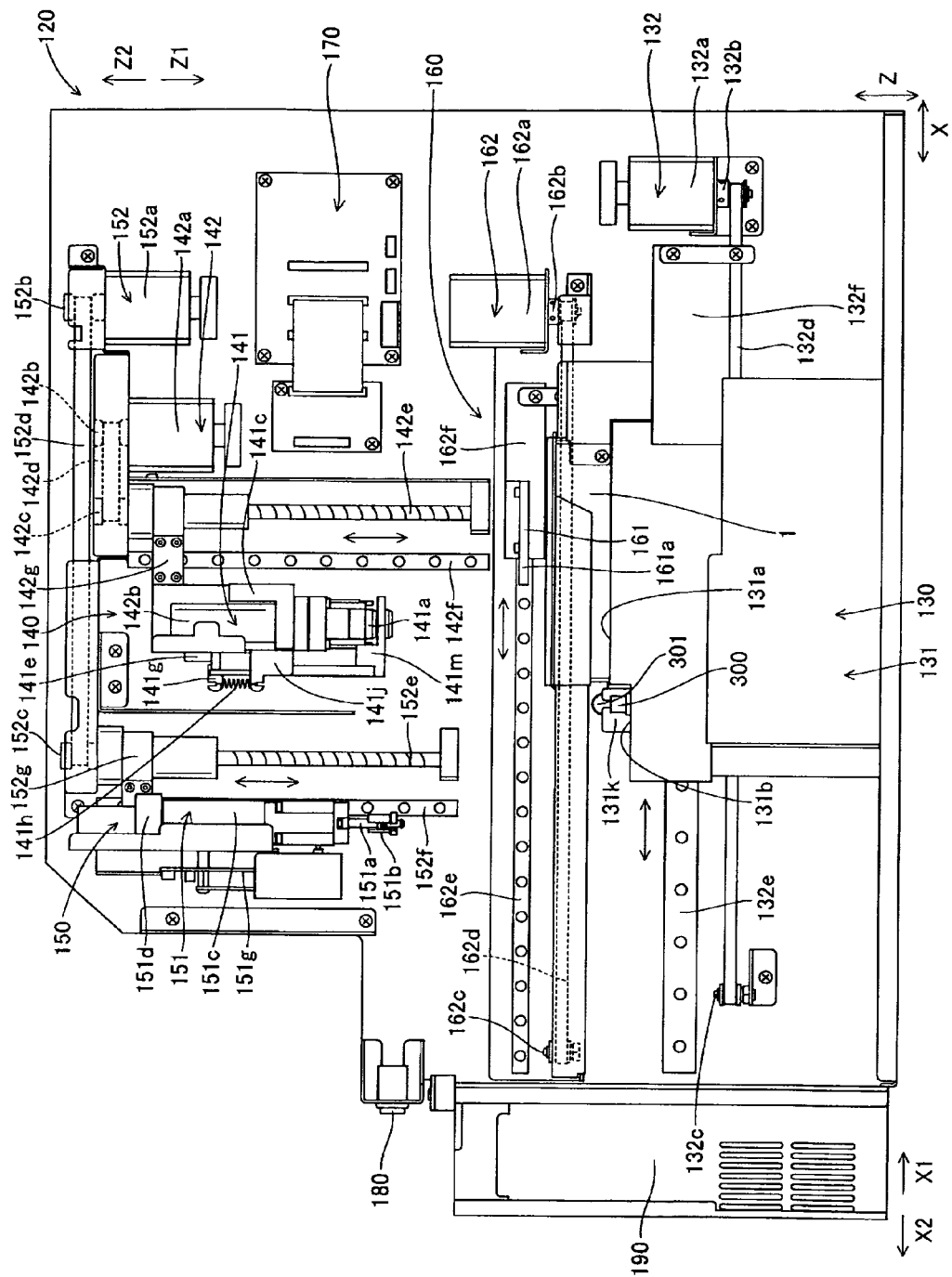

[Fig. 17]
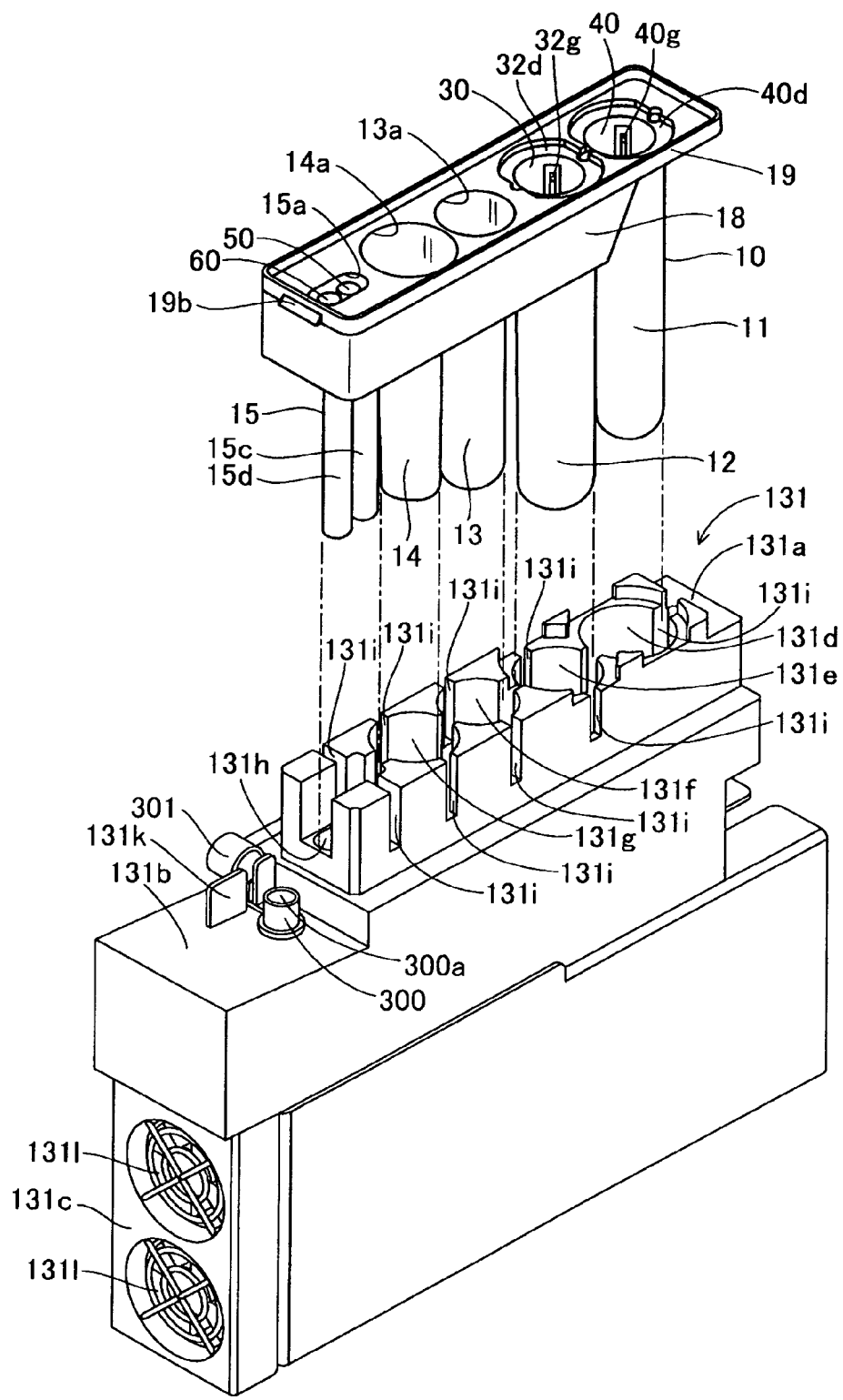

[Fig. 18]
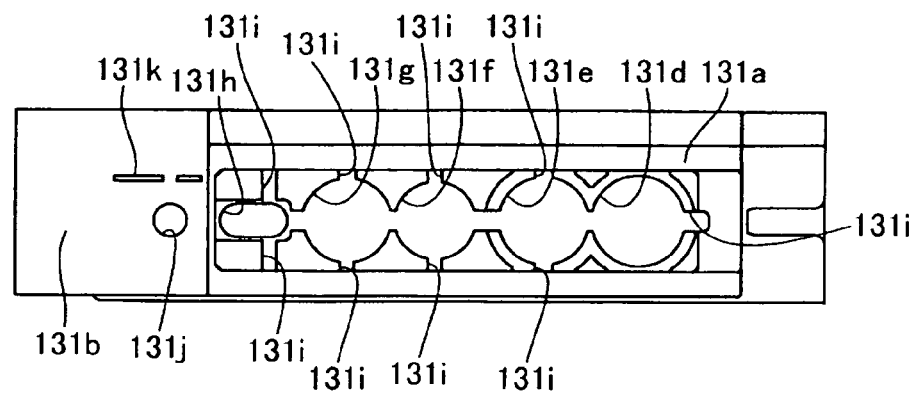
[Fig. 19]
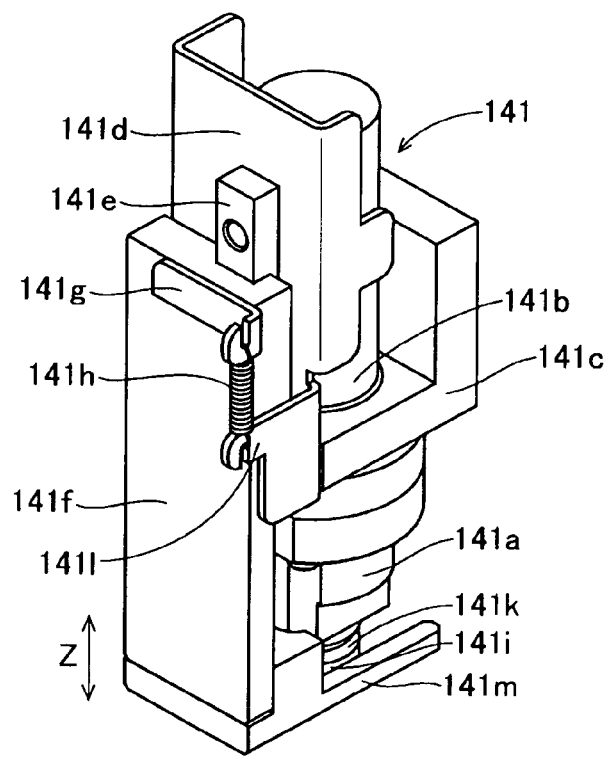

[Fig. 20]
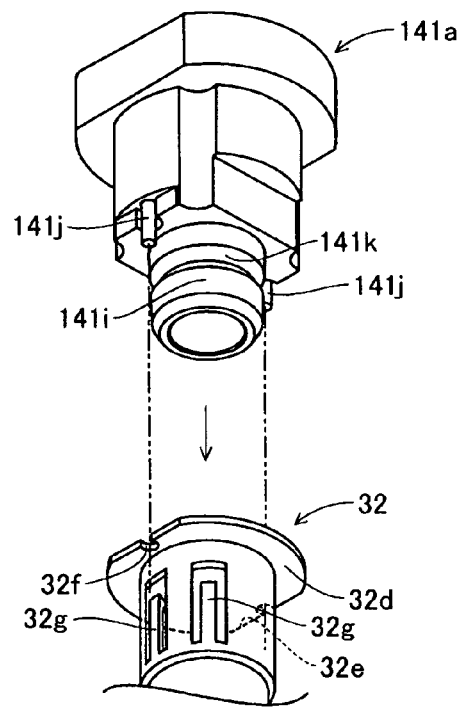
[Fig. 21]
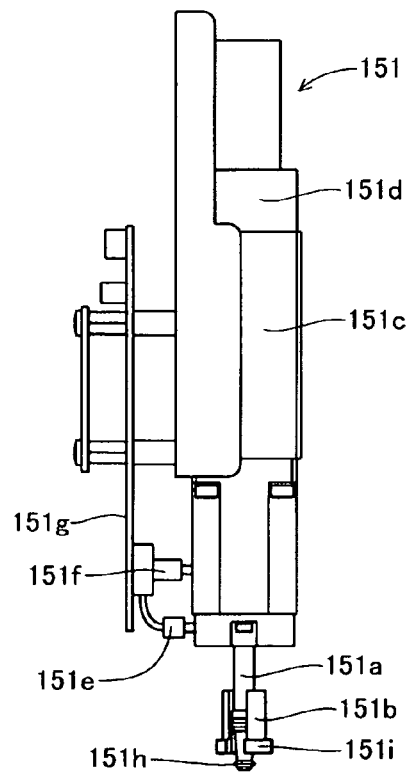

[Fig. 22]
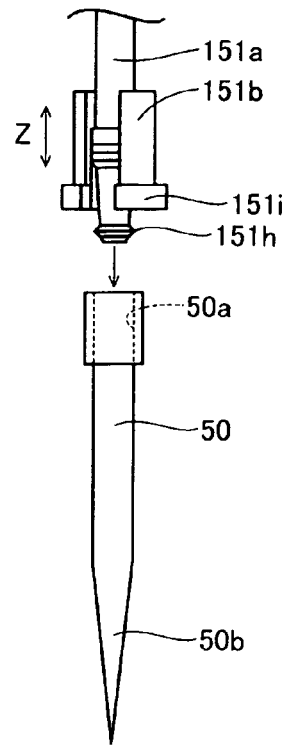
[Fig. 23]
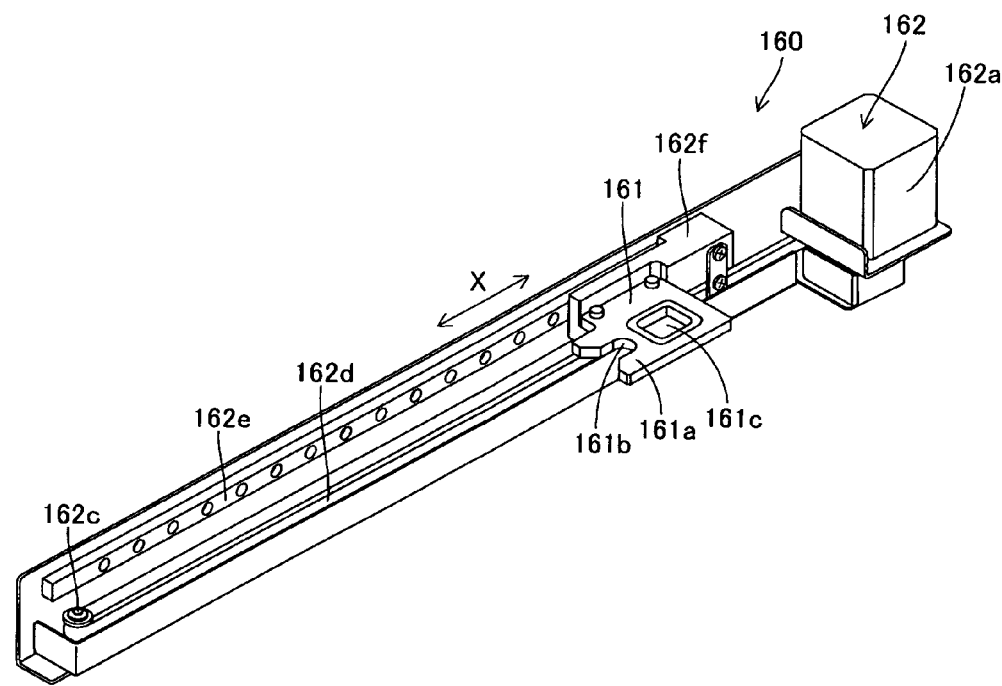

[Fig. 24]
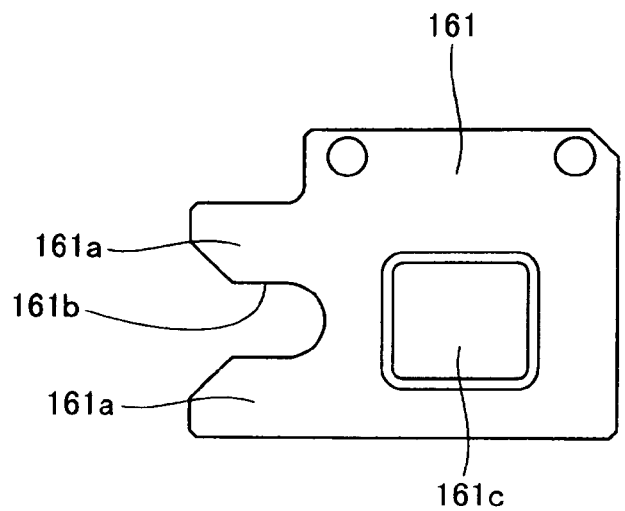
[Fig. 25]
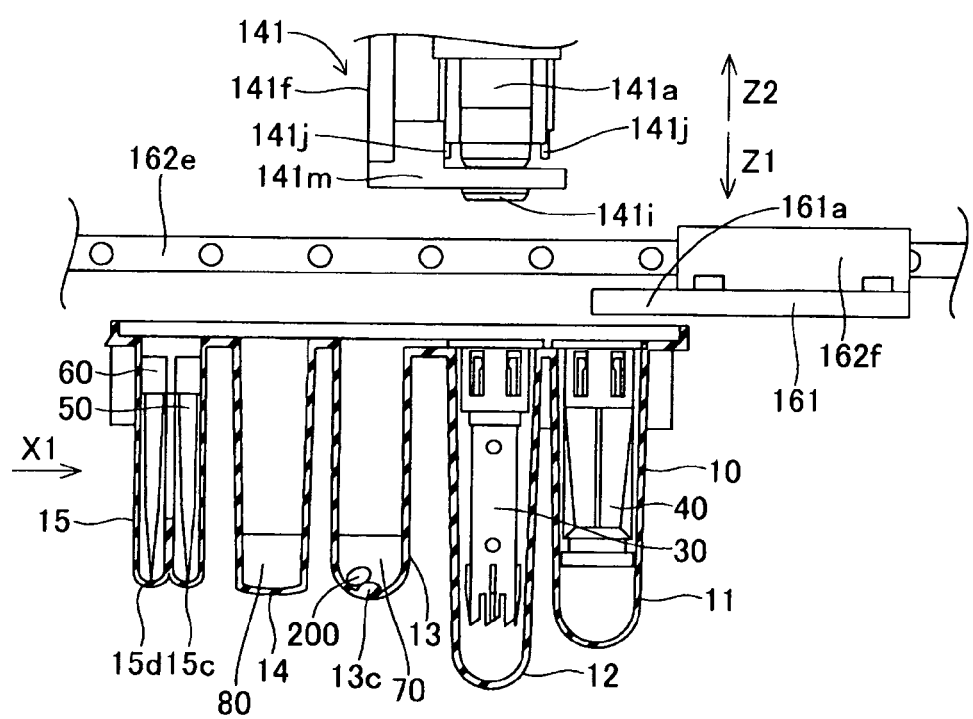

[Fig. 26]
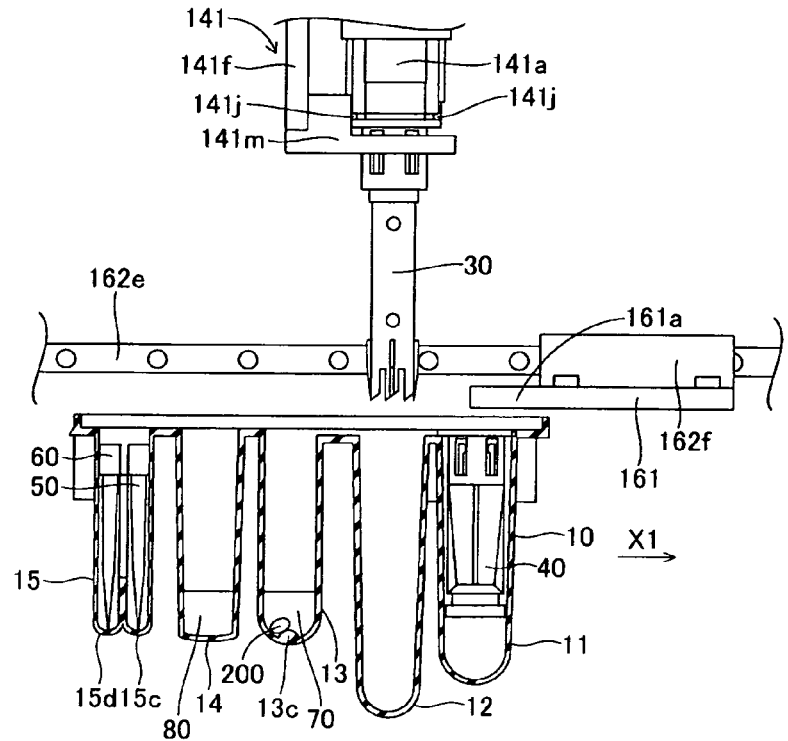
[Fig. 27]
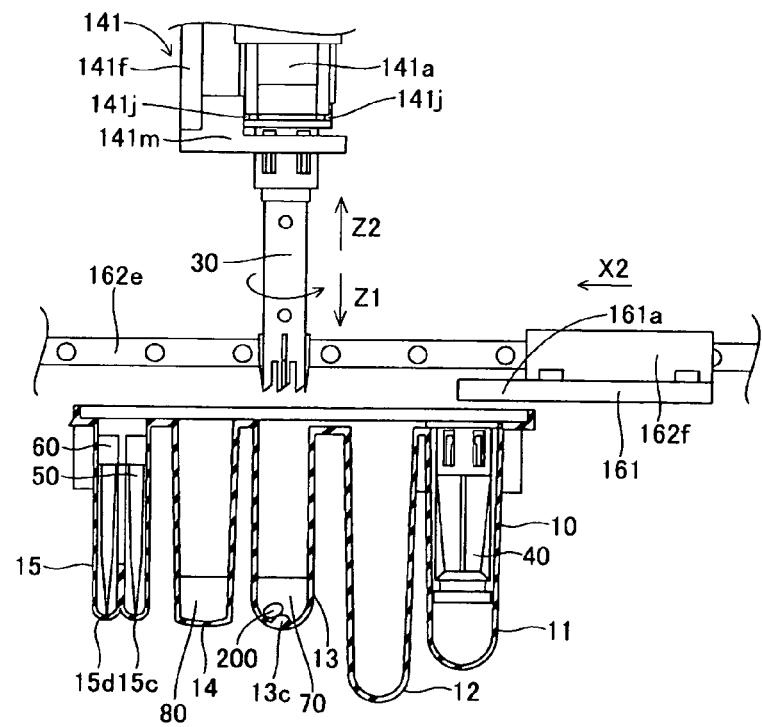

[Fig. 28]
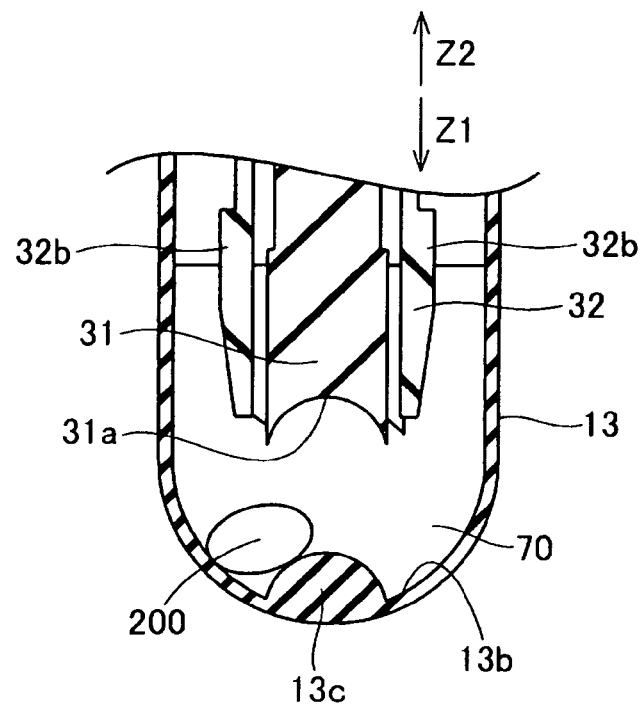
[Fig. 29]
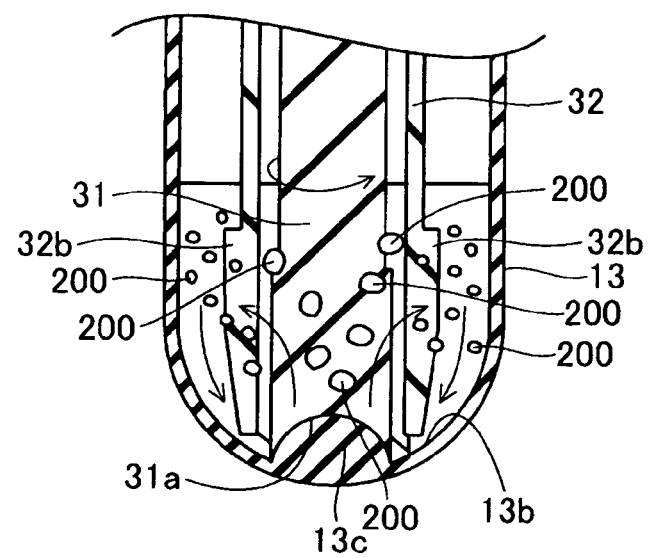

[Fig. 30]
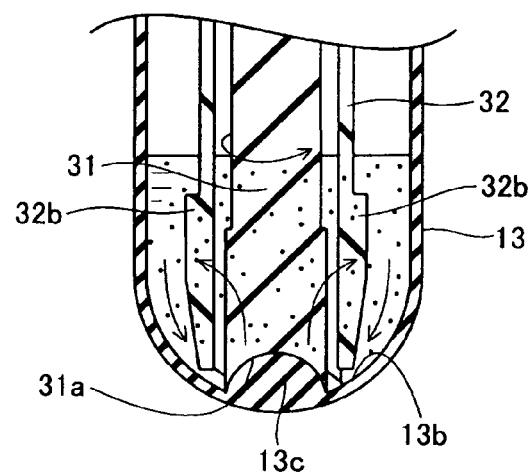
[Fig. 31]
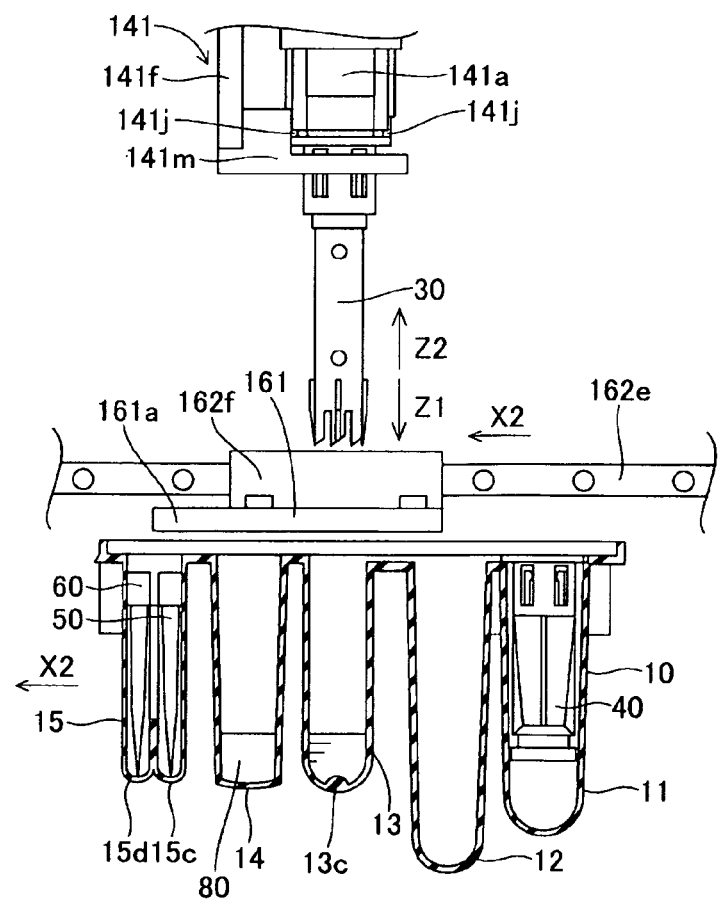

[Fig. 32]
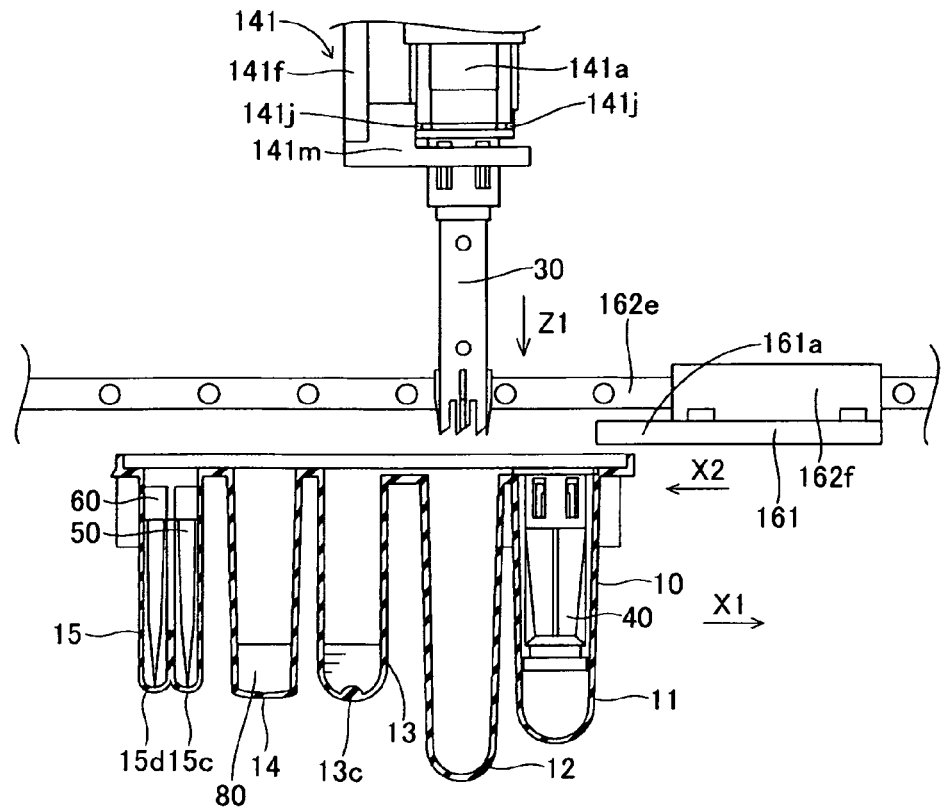
[Fig. 33]
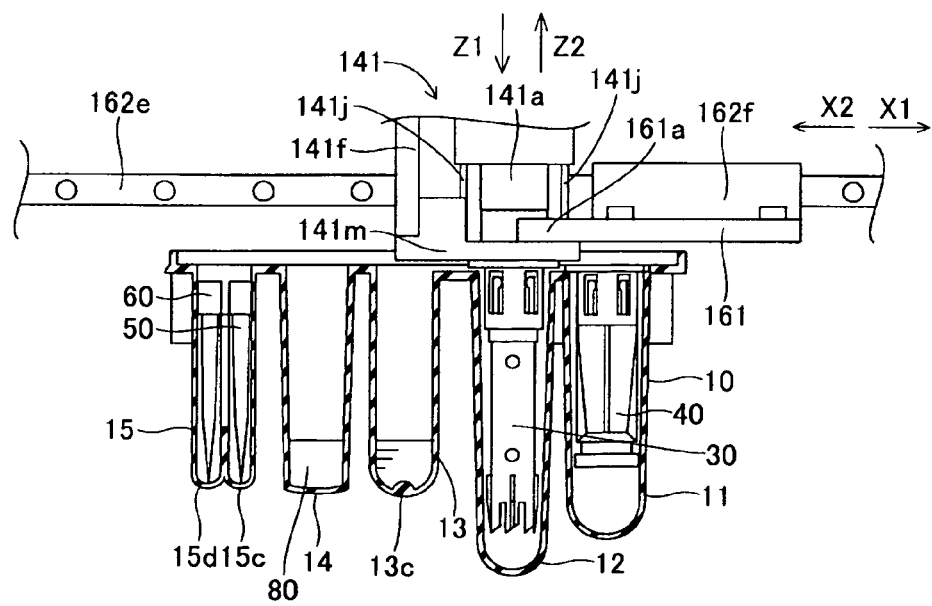

[Fig. 34]
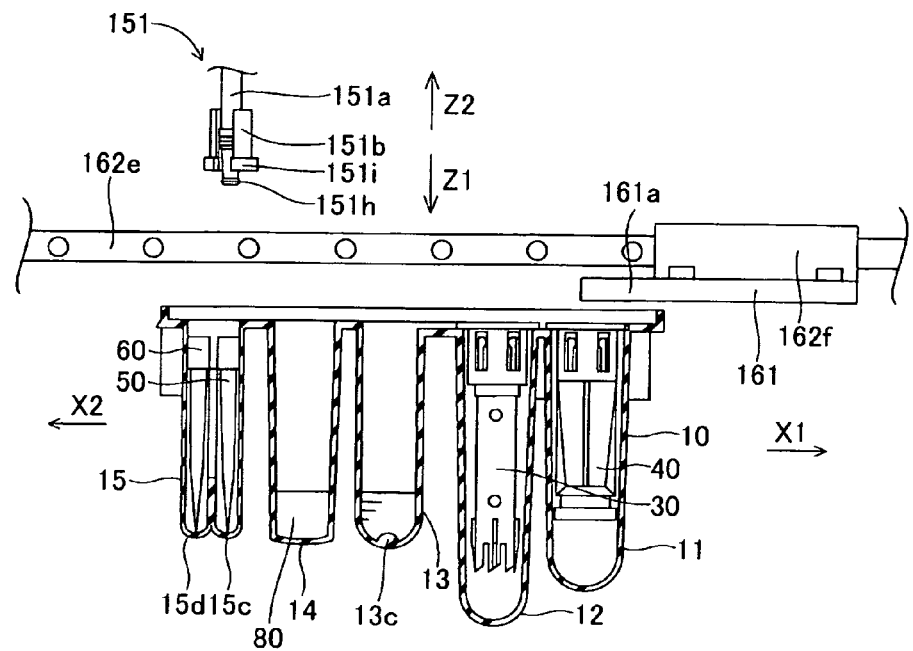
[Fig. 35]
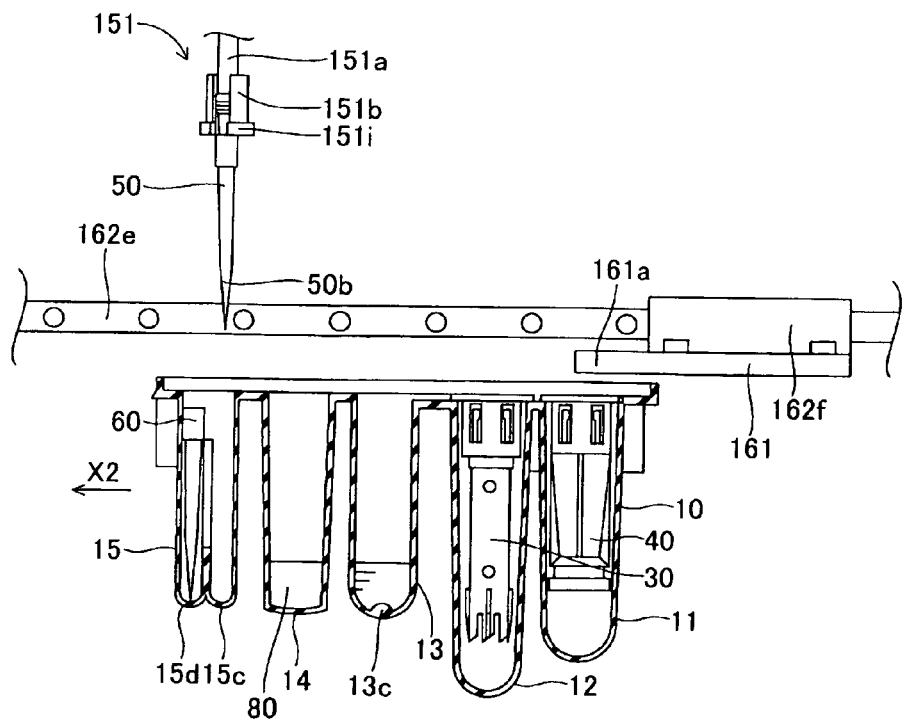

[Fig. 36]
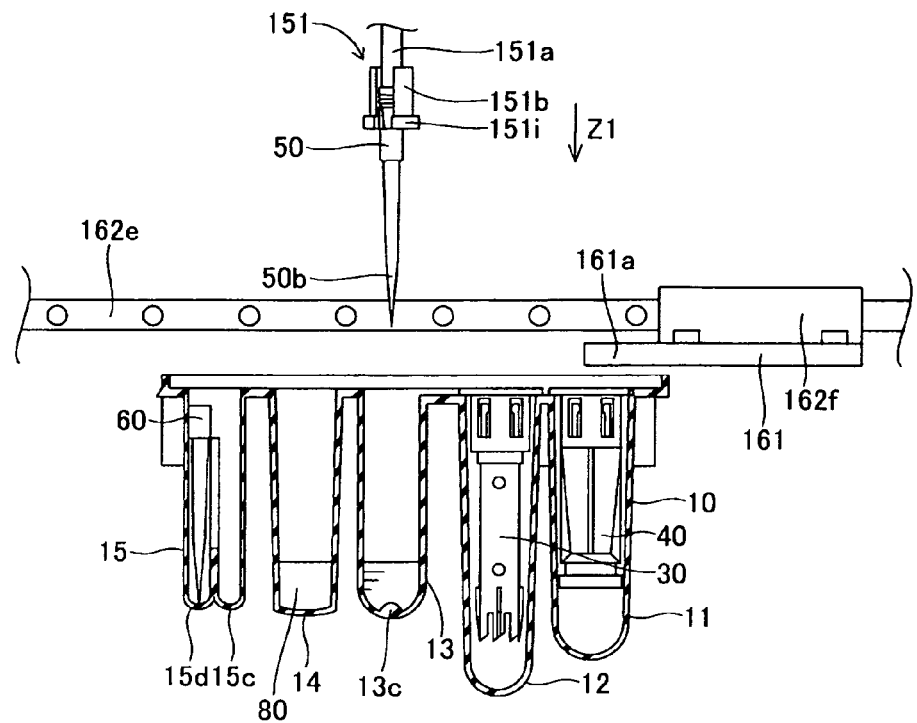
[Fig. 37]
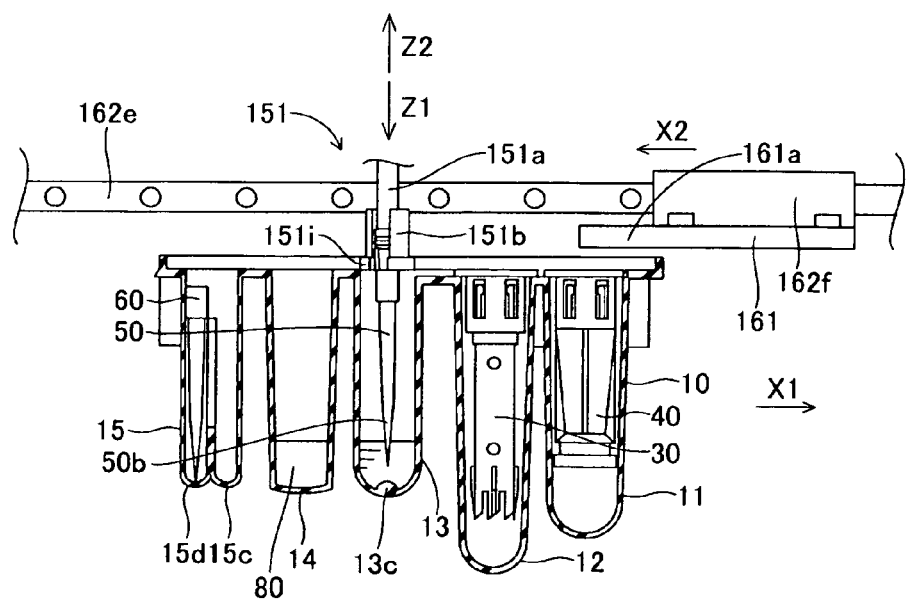

[Fig. 38]
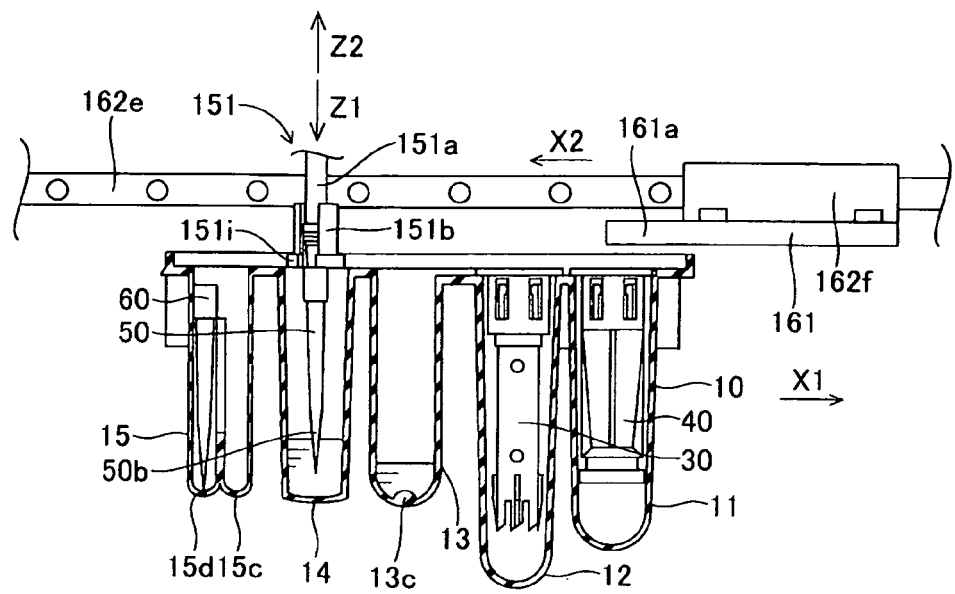
[Fig. 39]
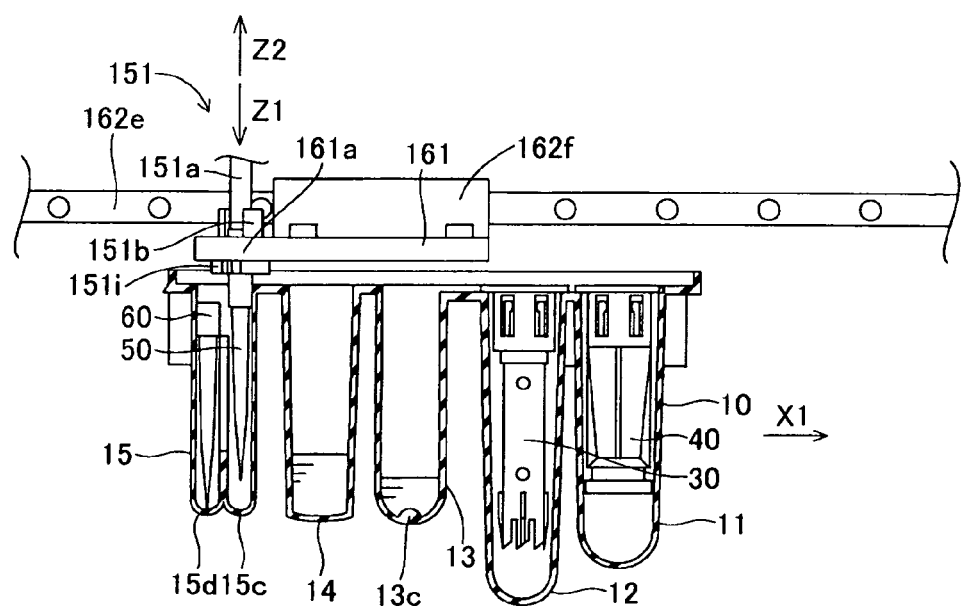

[Fig. 40]
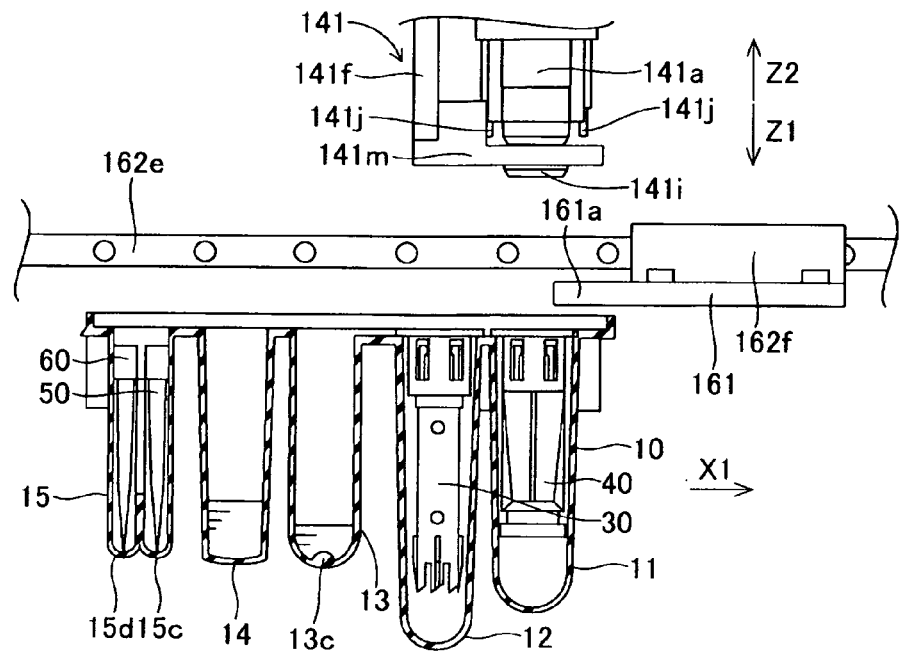
[Fig. 41]
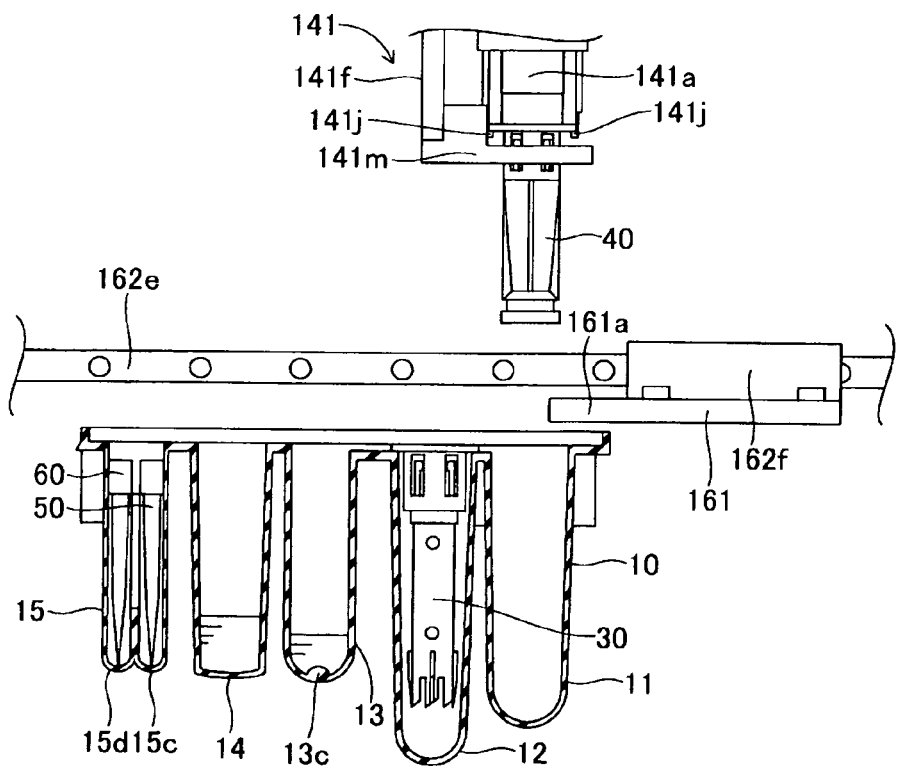

[Fig. 42]
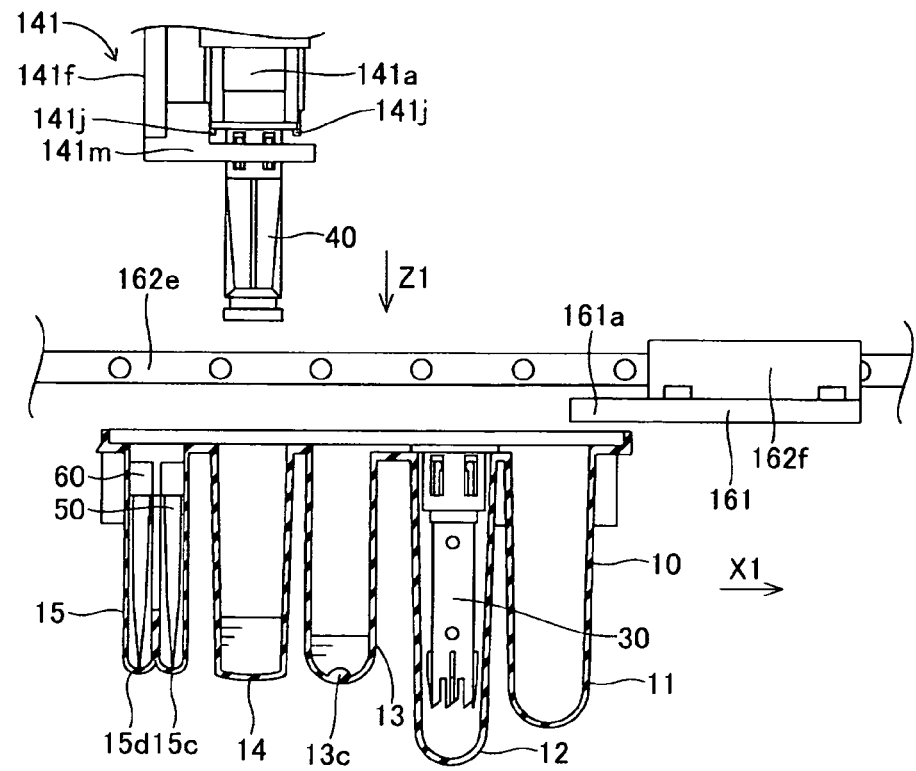
[Fig. 43]
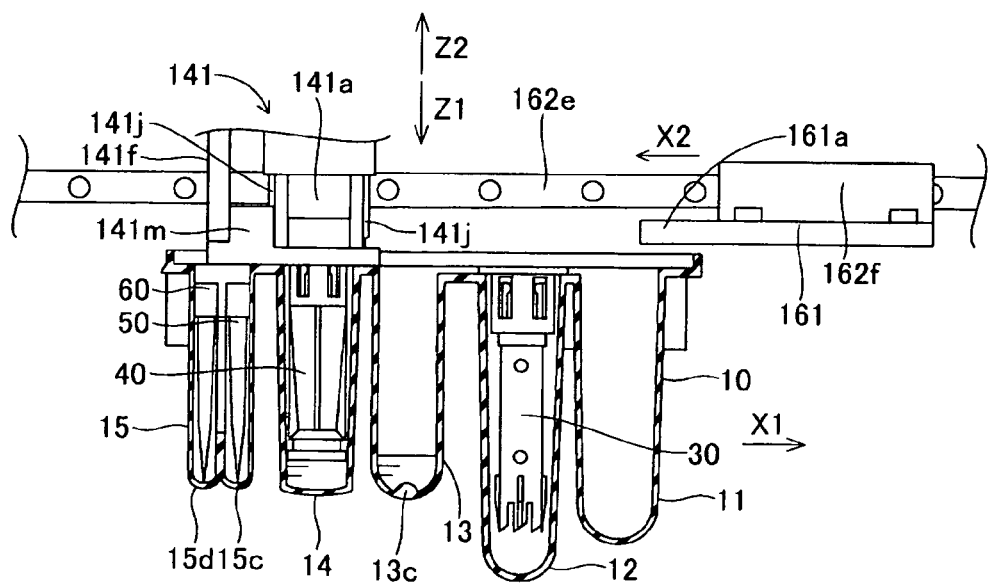

[Fig. 44]
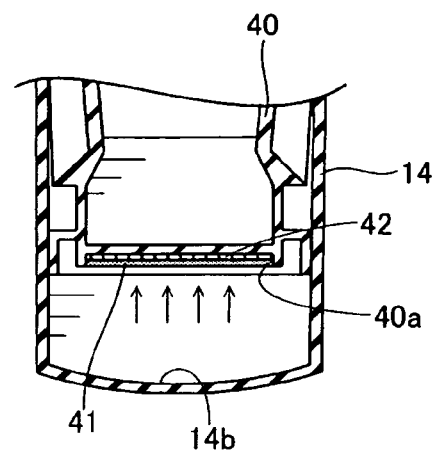
[Fig. 45]
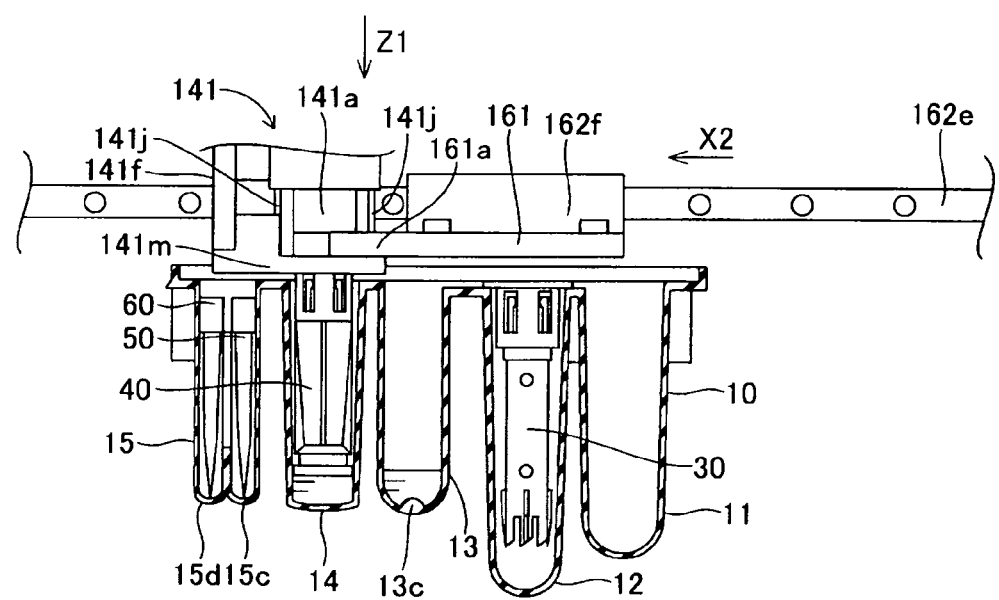

[Fig. 46]
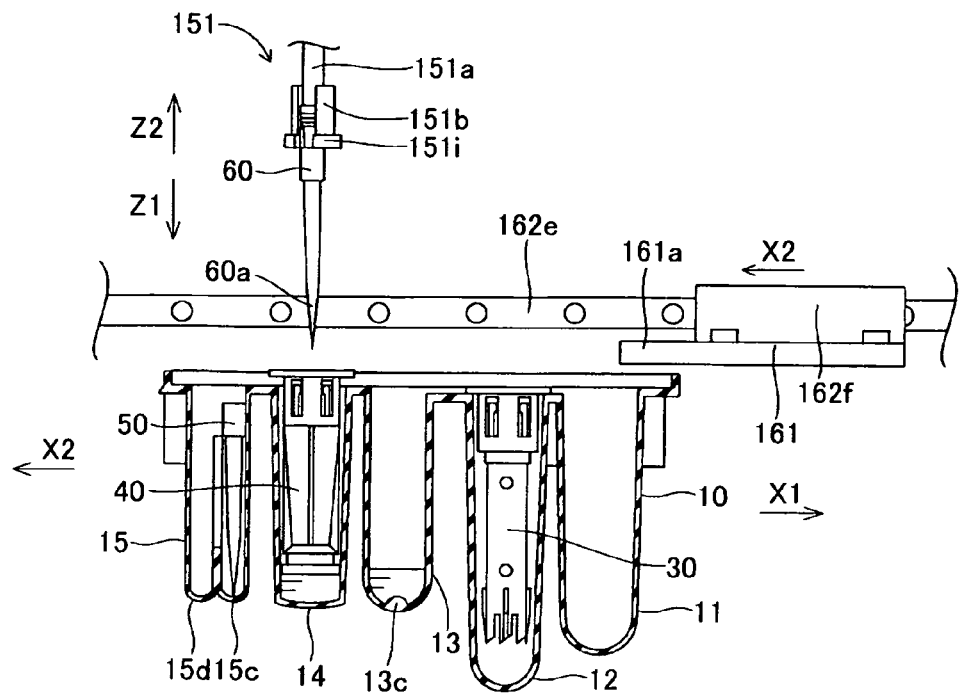
[Fig. 47]
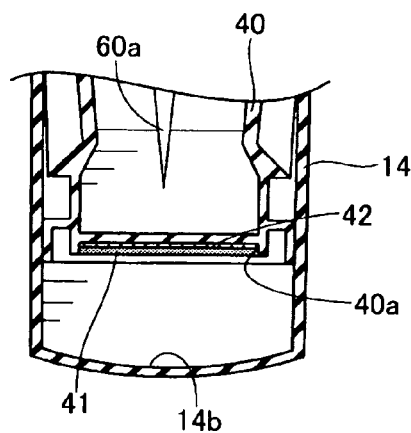

[Fig. 48]
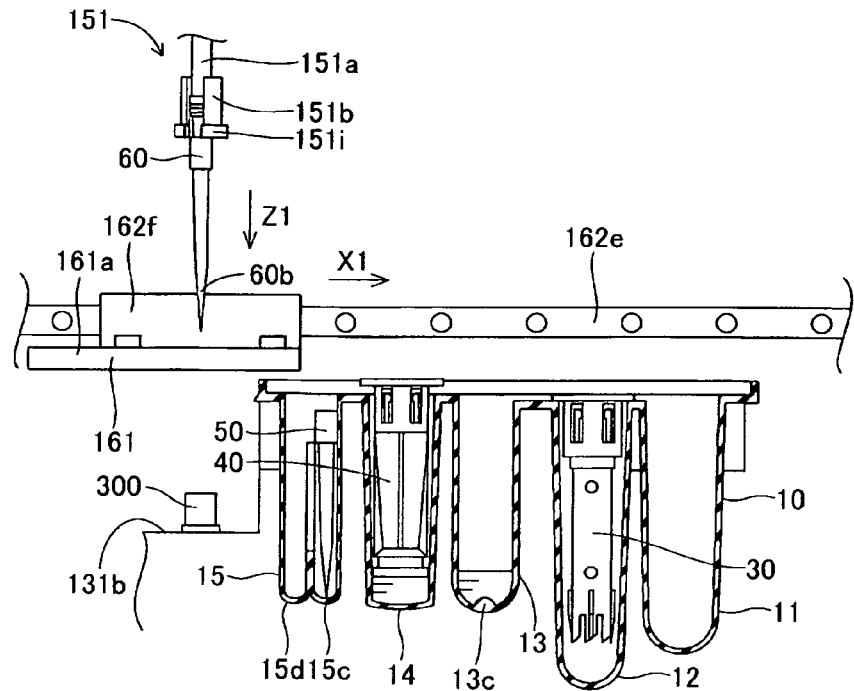
[Fig. 49]
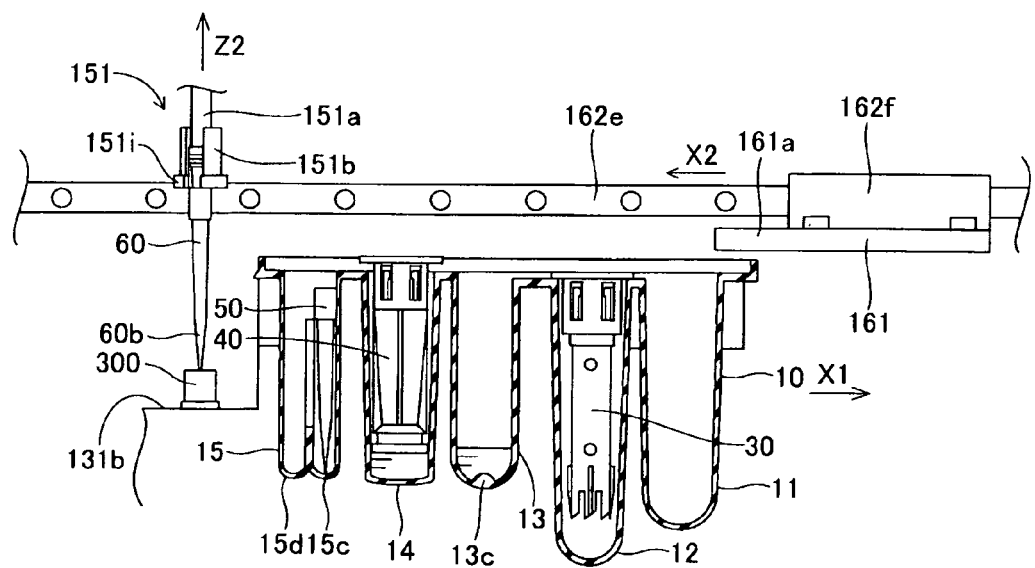

[Fig. 50]
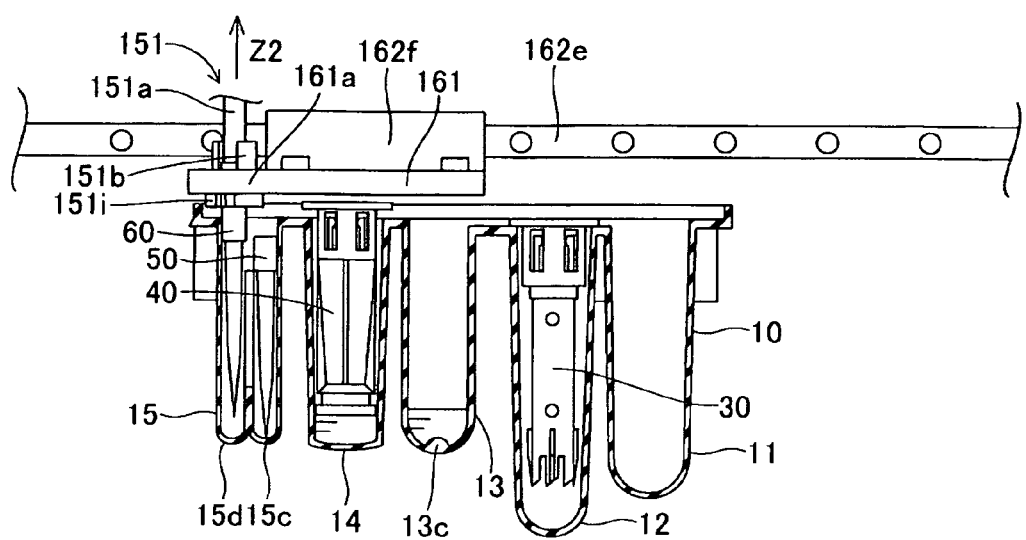

SAMPLE PREPARATION KIT, SAMPLE PREPARATION CONTAINER, AND SAMPLE PROCESSING DEVICE

FIELD OF THE INVENTION

The present invention relates to sample preparation kits and sample preparation containers, in particular, to a sample preparation kit and a sample preparation container including an accommodation chamber for crushing the body tissue. The present invention further relates to sample processing devices, in particular, to a sample processing device for processing the sample of the body tissue and the like.

BACKGROUND OF THE INVENTION

A sample machining device for thinly cutting the body tissue in the container by rotating a machining body, having a rough surface part formed with grooves on the surface and a machining body front end portion of convex shape complying with the shape of the tapered portion of the container, within the container formed with the tapered portion of concave shape having a shape in which the front end is pointed towards the lower part (bottom surface part) side is conventionally known (see e.g., JP-A No. 63-112974). Since the convex shape of the machining body front end portion of the machining body is formed into a shape that complies with the inner shape of the concave shape of the tapered portion of the container in this sample machining device, the body tissue is crushed with the groove of the rough surface part of the machining body functioning to cut the body tissue when the machining body is rotated.

However, in the sample machining device disclosed in JP-A No. 63-112974, it is difficult to completely match the convex shape of the machining body front end portion to the internal shape of concave shape of the tapered portion in terms of machining precision even if the convex shape of the machining body front end portion of the machining body is formed into a shape complying with the internal shape of concave shape of the tapered portion of the container. Thus, a space (dead space) where it is difficult to be reached by the machining body front end may form between the inner surface portion of concave shape of the front end of the tapered portion of the container and the machining body front end portion of convex shape of the machining body. As a result, it becomes difficult for the machining body front end portion of convex shape of the machining body to reach the body tissue that has entered the space formed at the front end of the container, and thus becomes difficult to crush the body tissue.

In a typical sample processing device (sample machining device), the sample is prepared by crushing the body tissue in a crushing solution for crushing the body tissue when crushing the body tissue in the container. However, in the sample machining device disclosed in Japanese Patent Application Laid-Open (JP-A) No. 63-112974, the crushing solution obtained from a predetermined region must be injected into the container where the body tissue is accommodated and then the machining body must be arranged in the relevant container to crush the body tissue accommodated in the container. The task of crushing the body tissue thus becomes complicated.

Although not disclosed in the sample machining device of JP-A No. 63-112974, normally, the crushing tool performed with heat killing for each time crushing of the body tissue is performed is obtained from a predetermined region, and the crushing tool must be mounted on a mechanism for rotatably supporting the crushing tool in order to crush the body tissue accommodated in the container. The task of crushing the body tissue thus becomes complicated.

Furthermore, although in JP-A No. 63-112974, extracting the filtrate from the sample obtained by crushing the body tissue is not disclosed, normally, after the sample obtained by crushing the body tissue is aliquoted, filtration is performed using the aliquot sample, and the filtrate is extracted. Thus, after aliquoting the sample obtained by crushing the body tissue, it must be dispensed to a filter device and the like capable of performing filtration in order to extract the filtrate in the sample machining device of JP-A No. 63-112974. As a consequence, the task of filtering the sample obtained form the body tissue thus becomes complicated.

Conventionally, a filter device including a filtering tool, a homogenizer (device for homogenizing the sample) including a crushing tool and the like are known as a sample processing device for processing the sample of the body tissue and the like (see e.g., U.S. Publication No. 5,282,978 and JP-A No. 2000-333669).

A filter device for filtering the tissue solution (suspension) including cell particles obtained by crushing the body tissue to collect only the cell particles larger than a predetermined size thereby manufacturing a specimen slide glass attached on the surface with cell particles larger than the predetermined size is disclosed in U.S. Pat. No. 5,282,978. The filtering tool of U.S. Pat. No. 5,282,978 is configured by a cylindrical body having one end opened and the other end arranged with a filter. In U.S. Pat. No. 5,282,978, first, the filtering tool is inserted into the container where the tissue solution is stored and then the internal part of the filtering tool is made to negative pressure to suction the tissue solution, in manufacturing the specimen slide glass. The filtrate is then extracted to the internal part of the filtering tool. The cell particles smaller than the predetermined size pass through the filter and move to the internal part of the filtering tool, whereas the cell particles larger than the predetermined size do not pass the filter and remain at the outer surface of the filter. Thereafter, the cell particles remaining at the outer surface of the filter are attached to the surface of the slide glass by contacting the outer surface of the filter of the filtering tool and the surface of the slide glass. The specimen slide glass is thereby manufactured.

A homogenizer for manufacturing the tissue solution containing the homogenized body tissue by performing homogenization on the body tissue with a crushing tool (passel) is disclosed in JP-A No. 2000-333669. Only homogenization of the body tissue is performed in the homogenizer disclosed in JP-A No. 2000-333669.

However, in the filter device of U.S. Publication No. 5282978, it becomes difficult to collect the filtrate when performing analysis and the like of the filtrate since the filtrate is extracted to the internal part of the filtering tool made of a cylindrical body having one end opened and the other end arranged with a filter.

Furthermore, in the homogenizer of JP-A No. 2000-333669, a filter device must be separately prepared when filtering the tissue solution since a mechanism for filtering the tissue solution is not arranged.

SUMMARY OF THE INVENTION

The scope of the present invention is defined solely by the appended claims, and is not affected to any degree by the statements within this summary.

The sample preparation kit according to a first aspect of the present invention includes: (a) a tissue container for containing tissue from a living body and comprising a convex part on an inner bottom of the container; and (b) a crushing tool for crushing the tissue contained in the tissue container by using the convex part.

The sample preparation kit according to a second aspect of the present invention includes: (a) a tissue container for containing tissue from a living body; and (b) a solution, for forming tissue homogenate, contained in the tissue container, wherein the tissue is crushed in the solution.

The sample preparation kit according to a third aspect of the present invention includes: (a) a filtering container for containing a tissue solution obtained by crushing tissue from a living body in a solution for forming tissue homogenate; and (b) a filtering tool for filtering the tissue solution in the filtering container The sample preparation kit according to a fourth aspect of the present invention includes: (a) a tissue container for containing tissue from a living body; (b) a solution, for forming tissue homogenate, contained in the tissue container, (c) a crushing tool holder for holding a crushing tool; (d) the crushing tool, for crushing the tissue in the solution, hold in the crushing tool holder; (e) a filtering container for filtering a tissue solution obtained by crushing the tissue in the tissue container; (f) a diluent, for diluting the tissue solution, contained in the filtering container; (g) a filtering toll holder for holding a filtering toll; (h) the filtering toll, for filtering the tissue solution in the filtering container, hold in the filtering toll holder; (i) a dispensing toll holder for holding a filtering toll; (j) the dispensing toll, for dispensing the tissue solution to the filtering container, hold in the dispensing toll holder; and (k) a joining part for joining the tissue container, the crushing tool holder, the filtering container, the filtering tool holder and the dispensing tool holder.

The sample preparation container according to a fifth aspect of the present invention includes: (a) a container for containing tissue from a living body and comprising a convex part on an inner bottom of the container for crushing the tissue.

The sample processing device according to a sixth aspect of the present invention includes: (a) a filtering toll mover assembly for moving a filtering toll for filtering a tissue solution obtained by crushing tissue from a living body in a solution for forming tissue homogenate, into a filtering container; and (b) a tissue solution suction assembly for suctioning a filtered tissue solution obtained by filtering the tissue solution by the filtering toll in the filtering container.

BRIEF DESCRIPTION OF THE DRAWINGS

The invention, together with objects and advantages thereof, may best be understood by reference to the following description of the presently preferred embodiments together with the accompanying drawings in which:

FIG. 1 is a perspective view showing the entire configuration of a sample processing device employing the sample preparation kit according to one embodiment of the present invention;

FIG. 2 is a perspective view of the sample preparation kit according to one embodiment of the present invention;

FIG. 3 is an exploded view of the sample preparation kit according to one embodiment shown in FIG. 2;

FIG. 4 is a perspective view showing a state in which the lid of the sample preparation kit according to one embodiment shown in FIG. 2 is removed;

FIG. 5 is a perspective view showing the sample preparation container of the sample preparation kit according to one embodiment shown in FIG. 2;

FIG. 6 is a plane view showing the sample preparation container of the sample preparation kit according to one embodiment shown in FIG. 2;

FIG. 7 is an enlarged front view showing a convex part of a crushing solution storing chamber of the sample preparation container of the sample preparation kit according to one embodiment shown in FIG. 2;

FIG. 8 is an enlarged plan view showing a convex part of a crushing solution storing chamber of the sample preparation container of the sample preparation kit according to one embodiment shown in FIG. 2;

FIG. 9 is an exploded view of a crushing tool of the sample preparation kit according to one embodiment shown in FIG. 2;

FIG. 10 is a front view of an inner side crushing member of the crushing tool of the sample preparation kit according to one embodiment shown in FIG. 2;

FIG. 11 is a plan view of an outer side crushing member of the crushing tool of the sample preparation kit according to one embodiment shown in FIG. 2;

FIG. 12 is a front view of a filtering tool of the sample preparation kit according to one embodiment shown in FIG. 2;

FIG. 13 is a cross sectional view of the filtering tool of the sample preparation kit according to one embodiment shown in FIG. 2;

FIG. 14 is a plan view of the filtering tool of the sample preparation kit according to one embodiment shown in FIG. 2;

FIG. 15 is a perspective view of the main body part of the sample processing device shown in FIG. 1;

FIG. 16 is a plan view of the main body part of the sample processing device shown in FIG. 1;

FIG. 17 is a perspective view showing a state in which the sample preparation kit according to one embodiment shown in FIG. 2 is installed in the installation part of the sample processing device;

FIG. 18 is a plan view of the installation part of the sample processing device shown in FIG. 1;

FIG. 19 is a perspective view of a holding part of the sample processing device shown in FIG. 1;

FIG. 20 is a perspective view showing a state in which the crushing tool of the sample preparation kit according to one embodiment shown in FIG. 2 is mounted to a blade mounting part of the holding part;

FIG. 21 is a front view of a syringe part of the sample processing device shown in FIG. 1;

FIG. 22 is a front view showing a state in which the dispensing chips of the sample preparation kit according to one embodiment shown in FIG. 2 are mounted to a nozzle part of the syringe part;

FIG. 23 is a perspective view of a dismounting mechanism section of the sample processing device shown in FIG. 1;

FIG. 24 is a plan view of a dismounting member of the dismounting mechanism section of the sample processing device shown in FIG. 1;

FIG. 25 is a view for explaining the operation of obtaining the filtrate of the sample processing device employing the sample preparation kit according to one embodiment of the present invention;

FIG. 26 is a view for explaining the operation of obtaining the filtrate of the sample processing device employing the sample preparation kit according to one embodiment of the present invention;

FIG. 27 is a view for explaining the operation of obtaining the filtrate of the sample processing device employing the sample preparation kit according to one embodiment of the present invention;

FIG. 28 is a cross sectional view for explaining the operation of crushing the lymph node by means of the crushing tool of the sample preparation kit according to one embodiment of the present invention shown in FIG. 2;

FIG. 29 is a cross sectional view for explaining the operation of crushing the lymph node by means of the crushing tool of the sample preparation kit according to one embodiment of the present invention shown in FIG. 2;

FIG. 30 is a cross sectional view for explaining the operation of crushing the lymph node by means of the crushing tool of the sample preparation kit according to one embodiment of the present invention shown in FIG. 2;

FIG. 31 is a view for explaining the operation of obtaining the filtrate of the sample processing device employing the sample preparation kit according to one embodiment shown in FIG. 2;

FIG. 32 is a view for explaining the operation of obtaining the filtrate of the sample processing device employing the sample preparation kit according to one embodiment shown in FIG. 2;

FIG. 33 is a view for explaining the operation of obtaining the filtrate of the sample processing device employing the sample preparation kit according to one embodiment shown in FIG. 2;

FIG. 34 is a view for explaining the operation of obtaining the filtrate of the sample processing device employing the sample preparation kit according to one embodiment shown in FIG. 2;

FIG. 35 is a view for explaining the operation of obtaining the filtrate of the sample processing device employing the sample preparation kit according to one embodiment shown in FIG. 2;

FIG. 36 is a view for explaining the operation of obtaining the filtrate of the sample processing device employing the sample preparation kit according to one embodiment shown in FIG. 2;

FIG. 37 is a view for explaining the operation of obtaining the filtrate of the sample processing device employing the sample preparation kit according to one embodiment shown in FIG. 2;

FIG. 38 is a view for explaining the operation of obtaining the filtrate of the sample processing device employing the sample preparation kit according to one embodiment shown in FIG. 2;

FIG. 39 is a view for explaining the operation of obtaining the filtrate of the sample processing device employing the sample preparation kit according to one embodiment shown in FIG. 2;

FIG. 40 is a view for explaining the operation of obtaining the filtrate of the sample processing device employing the sample preparation kit according to one embodiment shown in FIG. 2;

FIG. 41 is a view for explaining the operation of obtaining the filtrate of the sample processing device employing the sample preparation kit according to one embodiment shown in FIG. 2;

FIG. 42 is a view for explaining the operation of obtaining the filtrate of the sample processing device employing the sample preparation kit according to one embodiment shown in FIG. 2;

FIG. 43 is a view for explaining the operation of obtaining the filtrate of the sample processing device employing the sample preparation kit according to one embodiment shown in FIG. 2;

FIG. 44 is a cross sectional view showing a state in which the filtrate is extracted by the filtering tool of the sample preparation kit according to one embodiment shown in FIG. 2;

FIG. 45 is a view for explaining the operation of obtaining the filtrate of the sample processing device employing the sample preparation kit according to one embodiment shown in FIG. 2;

FIG. 46 is a view for explaining the operation of obtaining the filtrate of the sample processing device employing the sample preparation kit according to one embodiment shown in FIG. 2;

FIG. 47 is a view for explaining the operation of obtaining the filtrate of the sample processing device employing the sample preparation kit according to one embodiment shown in FIG. 2;

FIG. 48 is a view for explaining the operation of obtaining the filtrate of the sample processing device employing the sample preparation kit according to one embodiment shown in FIG. 2;

FIG. 49 is a view for explaining the operation of obtaining the filtrate of the sample processing device employing the sample preparation kit according to one embodiment shown in FIG. 2; and FIG. 50 is a view for explaining the operation of obtaining the filtrate of the sample processing device employing the sample preparation kit according to one embodiment shown in FIG. 2.

DETAILED DESCRIPTION OF THE PREFERRED EMBODIMENTS

The embodiments of the present invention will now be described based on the drawings.

FIG. 1 is a perspective view showing the entire configuration of a sample processing device employing the sample preparation kit according to one embodiment of the present invention. FIG. 2 is a perspective view of the sample preparation kit according to one embodiment of the present invention, and FIG. 3 is an exploded view of the sample preparation kit according to one embodiment shown in FIG. 2. FIGS. 4 to 14 are views for explaining the detailed configuration of the sample preparation kit according to one embodiment shown in FIG. 2.

The sample processing device 100 employing the sample preparation kit 1 according to one embodiment of the present invention is a device for obtaining the filtrate by crushing the body tissue and then filtering the tissue solution obtained from the crushed body tissue, as shown in FIG. 1. The lymph node is used for the body tissue. The lymph node cut in advance is accommodated in the sample preparation container 10 of the sample preparation kit 1 and then installed in the sample processing device 100 shown in FIG. 1. The configuration of the sample preparation kit 1 according to one embodiment will now be described in detail with reference to FIGS. 2 to 14.

The sample preparation kit 1 according to the present embodiment includes a sample preparation container 10, a lid 20 fitted into the sample preparation container 10, a crushing tool 30 for crushing the cut lymph node, a filtering tool 40 for filtering the tissue solution obtained from the lymph node, and two dispensing chips 50 and 60 for suctioning and discharging the filtrate filtered by the filtering tool 40, as shown in FIGS. 2 and 3. Crushing solution 70 and diluted solution 80 are accommodated in the sample preparation container 10 of the sample preparation kit 1 in advance. The crushing solution 70 and the diluted solution 80 contain nonionic surface-active agent for breaking the membrane protein contained in the lymph node. As shown in FIGS. 3 and 4, a film 90 made of aluminum is adhered to the upper surface part 17 (see FIGS. 5 and 6) of the sample preparation container 10 to prevent dust and the like from entering the crushing solution 70, the diluted solution 80 and the like from the outside. The sample preparation kit 1 is a disposable kit that is disposed after each use.

As shown in FIGS. 3 to 6, the sample preparation kit 10 includes a filtering tool accommodating chamber 11 for accommodating the filtering tool 40, a crushing tool accommodating chamber 12 for accommodating the crushing tool 30, a crushing process accommodating chamber 13 for accommodating the crushing solution 70, a filter process accommodating chamber 14 for accommodating the diluted solution 80, and a dispensing chip accommodating chamber 15 for accommodating the two dispensing chips 50 and 60. Each accommodating chamber 11 to 15 is integrally formed by way of a reinforcing rib 16 and the upper surface part 17, as shown in FIG. 6. The filtering tool accommodating chamber 11, the crushing tool accommodating chamber 12, the crushing process accommodating chamber 13, the filter process accommodating chamber 14, and the dispensing chip accommodating chamber 15 each has an opening 11a, 12a, 13, 14a, and 15a on one end, and a bottom surface part 11b, 12b, 13b, 14b, and 15b on the other end. As shown in FIGS. 3 and 6, the side surface part 18 formed so as to surround the periphery of each accommodating chamber 11 to 15, and the crushing tool accommodating chamber 12, the crushing process accommodating chamber 13, the filter process accommodating chamber 14, as well as the dispensing chip accommodating chamber 15 are coupled by the reinforcing rib 16 mentioned above. The reinforcing rib 16 is also arranged between the filtering tool accommodating chamber 11 and the crushing tool accommodating chamber 12, between the crushing tool accommodating chamber 12 and the crushing process accommodating chamber 13, between the crushing process accommodating chamber 13 and the filter process accommodating chamber 14, and between the filter process accommodating chamber 14 and the dispensing chip accommodating chamber 15. A rim part 19 that extends upward in the vertical direction is arranged at the top surface part 17 so as to surround the periphery of the top surface part 17, and projections 19a and 19b are respectively arranged on the outer surface of the filtering tool accommodating chamber 11 side and the dispensing chip accommodating chamber 15 side of the rim part 19.

As shown in FIG. 3, the filtering tool accommodating chamber 11 is arranged to accommodate the filtering tool 40 of the sample preparation kit 1, and the crushing tool accommodating chamber 12 is arranged to accommodate the crushing tool 30. The filtering tool accommodating chamber 11 and the crushing tool accommodating chamber 12 are respectively provided with a supporting surface part 11c and 12c having an oval shape when seen in a plane view that is depressed by a predetermined depth from the top surface part 17, as shown in FIGS. 5 and 6. Notches 11d and 11e are formed in the filtering tool accommodating chamber 11. Notches 12d and 12e are formed in the crushing tool accommodating chamber 12. The notch 11e on the crushing tool accommodating chamber 12 side of the filtering tool accommodating chamber 11 and the notch 12e on the filtering tool accommodating chamber 11 side of the crushing tool accommodating chamber 12 are formed so as to be communicated.

In the present embodiment, the crushing process accommodating chamber 13 is arranged to crush the lymph node by means of the crushing tool 30 received from the opening 13a, and the lymph node that is cut in advance is accommodated in the crushing process accommodating chamber 13 along with the crushing solution 70. In the sample preparation kit 1 according to the present embodiment, the lymph node is crushed in the crushing solution 70 and the tissue solution is obtained in the crushing process accommodating chamber 13. A convex part 13c of semicircular shape corresponding to the concave part 13a (see FIG. 9) of semicircular shape of the inner side crushing member 31 of flat plate shape of the crushing tool 30 to be hereinafter described is formed in the inner bottom surface of the bottom surface part 13b of the crushing process accommodating chamber 13, as shown in FIGS. 7 and 8. The convex part 13c has a rib shape of cross form when seen in a plane view. The convex part 13c and the concave part 31a of the inner side crushing member 31 sandwich and crush the lymph node of a predetermined size. The curvature radius of the surface of the convex part 13c is formed so as to have substantially the same curvature radius as the surface of the concave part 31a of the inner side crushing member 31 of the crushing tool 30. Furthermore, a gap 13d is formed between the concave part 31a arranged at the flat plate shaped front end part of the inner side crushing member 31 and the portion other than the convex part 13c of rib shape of cross form when the concave part 31a arranged at the flat plate shaped front end part of the inner side crushing member 31 of the crushing tool 30 is rotated with respect to the convex part 13c of rib shape of cross form, as shown in FIG. 8.

In the present embodiment, the filter process accommodating chamber 14 is arranged to receive the tissue solution obtained by crushing the lymph node and filtering the received tissue solution. In the sample preparation kit 1 according to the present embodiment, the tissue solution obtained in the crushing tool accommodating chamber 13 is aliquoted, and the aliquot tissue solution is diluted with the diluted solution 80 accommodated in advance, in the filter process accommodating chamber 14. The filtrate is obtained by filtering the diluted tissue solution. The filter process accommodating chamber 14 is formed so that the cross sectional area of the opening gradually decreases from the opening 14a side towards the bottom surface part 14b side, as shown in FIGS. 3 and 6.

The dispensing chip accommodating parts 15c and 15d are formed in the dispensing chip accommodating chamber 15 so as to accommodate the dispensing chip 50 and 60, respectively.

As shown in FIGS. 2 and 3, the lid 20 is configured so as to be fitted into the sample preparation container 10. Specifically, an engagement hole 20a corresponding to the projection 19a arranged on the filtering tool accommodating chamber 11 side of the rim part 19 of the sample preparation container 10, and an engagement hole 20b corresponding to the projection 19b arranged on the dispensing chip accommodating chamber 15 side are formed in the lid 20. The lid 20 can be fitted into the sample preparation container 10 as the projections 19a and 19b of the sample preparation container 10 engage with the engagement holes 20a and 20b of the lid 20. The lid 20 also includes a concave part 20c formed so as to correspond to the opening 13a of the crushing process accommodating chamber 13. The concave part 20c corresponding to the opening 13a of the crushing process accommodating chamber 13 has a function of blocking the opening 13a of the crushing process accommodating chamber 13 when the lid 20 is fitted into the sample preparation container 10. Thus, the residual tissue solution is suppressed from leaking from the opening 13a of the crushing process accommodating chamber 13 with the lid 20 fitted into the sample preparation container 10 after aliquoting the tissue solution.

The crushing tool 30 is a housing configured by an inner side crushing member 31 and an outer side crushing member 32 made up of a cylindrical body capable of accommodating the inner side crushing member 31 therein, as shown in FIGS. 9 and 10. The crushing tool 30 is arranged to crush the lymph node accommodated with the crushing solution 70. Furthermore, the inner side crushing member 31 includes a concave part 31a formed at the front end part of flat plate shape so as to correspond to the convex part (see FIGS. 7 and 8) of the crushing process accommodating chamber 13 of the sample preparation container 10. The surface of the concave part 31a arranged at the front end part of flat plate shape is formed so as to have a curvature radius of substantially the same curvature radius as the surface of the convex part 13c of the crushing process accommodating chamber 13, as described above. A supporting part 31b to be gripped by the gripping part of the sample processing device 100, to be hereinafter described, is arranged on the side opposite the front end part side formed with the concave part 31a of the inner side crushing member 31. A plurality of blade parts 32a, a rib part 32b formed so as to project to the outer side from the outer peripheral surface side, and a plurality of slits 32c formed between the plurality of blade parts 32a are arranged on the lower part side of the outer side crushing member 32, as shown in FIG. 9. A collar part 32d having an oval shape corresponding to the supporting surface part 12c (see FIGS. 5 and 6) of oval shape of the crushing tool accommodating chamber 12, an opening 32e for accommodating the inner side crushing member 31 on the inside, two notches 32f, and a plurality of (four in the present embodiment) engagement nails 32g that can be bent and deformed are formed on the upper part side of the outer side crushing member 32, as shown in FIGS. 9 and 11. The two notches 32f are formed so as to correspond to the notches 12d and 12e formed in the crushing tool accommodating chamber 12 (see FIGS. 5 and 6).

The filtering tool 40 is arranged to filter the tissue solution obtained from the crushed lymph node, and is used to obtain the filtrate filtered through two filters 41 and 42 (see FIG. 13). The filtering tool 40 has a cylindrical shape, and is formed with a filter installation part 40a for arranging the two filters 41 and 42, and a sealing material installation part 40b on the lower part side. Although the sealing material is not arranged in the sealing material installation part 40b in the present embodiment, the sealing material can be arranged. As shown in FIG. 14, a filter supporting part 40c of cross form when seen in plan view is formed in the filter installation part 40a. The tissue solution is extracted to the inside of the filtering tool 40 through the gap 43 other than the portion formed with the filter supporting part 40c of the filter installation part 40a. As shown in FIGS. 12 and 14, the upper part side of the filtering tool 40 has a configuration similar to the upper part side of the outer side crushing member 32 described above, and is formed with a collar part 40d having an oval shape formed so as to correspond to the supporting surface part 11c (see FIGS. 5 and 6) of oval shape of the filtering tool accommodating chamber 11, an opening 40e, two notches 40f, and a plurality of (four in the present embodiment) engagement nails 40g that can be bent and deformed. The notch 40f is formed so as to correspond to the notches 11d and 11e (see FIGS. 5 and 6) formed in the filtering tool accommodating chamber 11.

The dispensing chip 50 accommodated in the dispensing chip accommodating part 15c is arranged to suction and discharge the tissue solution obtained from the crushed lymph node. The dispensing chip 60 accommodated in the dispensing chip accommodating part 15d is arranged to suction and discharge the filtrate obtained by filtering the tissue solution. The dispensing chip 50 has an opening 50a, and a front end part 50b on the side opposite the opening 50a, as shown in FIG. 3. Similarly, the dispensing chip 60 has an opening 60a, and a front end part 60b on the side opposite the opening 60a.

FIGS. 15 and 16 are perspective view and plan view, respectively, of the main body part of sample processing device shown in FIG. 1. FIGS. 17 to 24 are views showing a detailed configuration of each part of the sample processing device shown in FIG. 1. The configuration of the sample processing device 100 employing the sample preparation kit 1 of one embodiment will now be described in detail with reference to FIGS. 1, 3, 6, 9, 10, 12, and 14 to 24. The sample processing device 100 is configured so that the filtrate can be obtained by performing a predetermined process on the accommodated lymph node after removing the lid 20 (see FIG. 3) and the film 90 (see FIG. 3), and installing the sample preparation kit 1 with the lymph node cut in advance accommodated therein. The sample processing device 100 is configured by a display part 110 for displaying predetermined information, and three main boy parts 120, as shown in FIG. 1. As shown in FIGS. 15 and 16, the main body part 120 is configured by a conveying mechanism section 130, a sample processing mechanism section 140, a suctioning and dispensing mechanism section 150, a removal mechanism section 160, and a control section 170. An eject button 180 is arranged on the sample process device 100. The installation part 131 of the conveying mechanism section 130 is moved in the X1 direction and conveyed to the outside from the door 190 by pushing the eject button 180. The sample preparation kit 1 can thus be installed in the sample processing device 100.

The conveying mechanism section 130 is configured by an installation part 131 and a movement mechanism part 132. The conveying mechanism section 130 has a function of installing the above described sample preparation kit 1 and also has a function of moving the sample preparation kit 1 in the X direction.

The installation part 131 is arranged to install the sample preparation kit 1, and to install a collection container 300 for accommodating the filtrate filtered by the filtering tool 40. The installation part 131 is configured by a kit installation part 131a for installing the sample preparation kit 1, a collection container installation part 131b for installing the collection container 300, and a temperature controlling part 131c (see FIG. 17) for controlling the tissue solution stored in the sample preparation kit 1 and the filtrate accommodated in the collection container 300 to a predetermined temperature, as shown in FIGS. 17 and 18.

The kit installation part 131a is provided with inserting parts 131d, 131e, 131f, 131g and 131h for respectively accommodating the filtering tool accommodating chamber 11, the crushing tool accommodating chamber 12, the crushing process accommodating chamber 13, the filter process accommodating chamber 14, and the dispensing chip accommodating chamber 15 of the sample preparation container 10. The kit installation part 131a is further provided with a rib inserting groove 131i formed so as to correspond to the reinforcing rib 16 of the sample preparation container 10.

The collection container installation part 131b includes a container inserting hole 131j for installing the collection container 300 (see FIG. 18) and a lid holding part 131k arranged to prevent the lid 301 attached to the collection container 300 from blocking the opening 300a of the collection container 300. Two fans 1311 are arranged and a Peltier element (not shown) is incorporated in the temperature controlling part 131c, where the two fans 1311 and the Peltier element are controlled based on the control signal transmitted from the controlling section 170 (see FIGS. 15 and 16) to be hereinafter described.

The movement mechanism part 132 is arranged to move the installation part 131 arranged with the sample preparation kit 1 in the X direction, as shown in FIGS. 15 and 16. The movement mechanism part 132 is configured by a motor 132a, a pulley 132b connected to the motor 132a, a pulley 132c arranged at a predetermined interval from the pulley 132b, a drive transmission belt 132d mounted to the pulley 132b and the pulley 132c, a direct acting guide 132e arranged so as to extend in the X direction, and a moving member 132f attached so as to be movable along the direct acting guide 132e and coupled to the drive transmission belt 132d. When the motor 132a is driven, the drive transmission belt 132d is driven by way of the pulley 132b, whereby the moving member 132f coupled to the drive transmission belt 132d moves in the X direction. The installation part 131 attached to the moving member 132f moves along the direct acting guide 132e with the moving member 132f.

The sample processing mechanism section 140 has a function of crushing the lymph node accommodated in the sample preparation kit 1 and filtering the tissue solution obtained through crushing using the crushing tool 30 (see FIG. 9) and the filtering tool 40 (see FIG. 12) accommodated in the sample preparation kit 1. The sample processing mechanism section 140 is configured by a holding part 141 and a movement mechanism part 142.

The holding part 141 has a function of holding the crushing tool 30 and the filtering tool 40 of the sample preparation kit 1. The holding part 141 includes a mounting part 141a for mounting the crushing tool 30 and the filtering tool 40, a motor 141b arranged on the upper part side of the mounting part 141a, an installation part 141c for installing the motor 141b and the mounting part 141a, a steel plate 141d attached to the installation part 141c, a direct acting guide 141e attached to the steel plate 141d, a moving member 141f attached so as to be movable along the direct acting guide 141e, a hook member 141g attached to the moving member 141f, and a spring 141h, as shown in FIG. 19.

As shown in FIG. 20, the mounting part 141a includes a press-fit part 141i press fitted from the opening 32e side of the outer side crushing member 32 of the crushing tool 30 and the opening 40e (see FIG. 14) side of the filtering tool 40, and a projection 141j for engaging the notch 32f of the outer side crushing member 32 of the crushing tool 30 and the notch 40f (see FIG. 14) of the filtering tool 40. The press-fit part 141i is provided with a groove 141k engaged with the engagement nail 32g of the outer side crushing member 32 of the crushing tool 30 and the engagement nail 40g (see FIG. 12) of the filer tool 40. The crushing tool 30 and the filtering tool 40 can be reliably held at the mounting part 141a since the press-fit part 141i of the mounting part 141a is press fitted to the opening 32e of the outer side crushing member 32 and the opening 40e of the filtering tool 40, and the engagement nail 32g and the engagement nail 40g engage with the groove 141k of the press-fit part 141i. Since the projection 141j of the mounting part 141a engages with the notch 32f of the outer side crushing member 32 and the notch 40f of the filtering tool 40, the outer side crushing member 32 and the filtering tool 40 are suppressed from rotating with respect to the mounting part 141a. Furthermore, a gripping part (not shown) that rotates with the drive of the motor 141b shown in FIG. 19 is arranged inside the press-fit part 141i, which gripping part has a function of rotatably gripping the supporting part 31b (see FIGS. 9 and 10) of the inner side crushing member 31 of the crushing tool 30. Therefore, the motor 141b functions as a driving source of rotating the inner side crushing member 31 of the crushing tool 30.

As shown in FIG. 19, a hook part 141l for attaching one end of the spring 141h is integrally formed in the steel plate 141d attached to the installation part 141c. The other end of the spring 141h is attached to the hook member 141g. Thus, the moving member 141f can be moved in the Z direction so as to follow the movement of the mounting part 141a in the Z direction. A abutting part 141m made of resin that contacts the release nail 161a of a dismounting member 161 of the dismounting mechanism section 160 to be hereinafter described is attached to the moving member 141f. The abutting part 141m is attached to the moving member 141f so as to abut against the collar part 32d (see FIG. 9) of the outer side crushing member 32 and the collar part 40d of the filtering tool 40 when the crushing tool 30 and the filtering tool 40 are mounted to the mounting part 141a.

The movement mechanism part 142 is arranged to move the holding part 141 in the Z direction, as shown in FIGS. 15 and 16. The movement mechanism part 142 is configured by a motor 142a, a pulley 142b connected to the motor 142a, a pulley 142c arranged at a predetermined interval from the pulley 142b, a drive transmission belt 142d mounted to the pulley 142b and the pulley 142c, a ball screw 142e that rotates with the rotation of the pulley 142c and that is arranged so as to extend in the Z direction, a direct acting guide 142f arranged so as to extend in the Z direction, and a moving member 142g that moves with the rotation of the ball screw 142e and that is attached so as to be movable along the direct acting guide 142f. With this configuration, when the motor 142a is driven, the drive transmission belt 142d is driven by way of the pulley 142b, whereby the pulley 142c mounted with the drive transmission belt 142d rotates. Since the ball screw 142e is rotated with the rotation of the pulley 142c, the moving member 142g that moves with the rotation of the ball screw 142e moves along the Z direction along which the direct acting guide 142f extends.

A suctioning and dispensing mechanism section 150 has a function of suctioning and dispensing the tissue solution and suctioning and dispensing the filtrate extracted from the tissue solution by mounting the dispensing chips 50 and 60 (see FIG. 3) of the sample preparation kit 1. The suctioning and dispensing mechanism section 150 is configured by a syringe part 151 for suctioning and discharging the tissue solution or the filtrate, and a movement mechanism part 152 for moving the suctioning and dispensing mechanism section 150 in the Z direction.

As shown in FIGS. 21 and 22, the syringe part 151 includes a nozzle part 151a to be attached with the dispensing chips 50 and 60 (see FIG. 3), a cap 151b made of resin attached to the nozzle part 151a, a pump part 151c for performing suction and discharge, a motor 151d that acts as a driving source of the pump part 151c, a liquid level detection sensor 151e for detecting whether or not the front end part 50b of the dispensing chip 50 and the front end part 60b of the dispensing chip 60 are contacting the liquid level, a pressure detection sensor 151f for detecting the pressure in time of suction and discharge by the pump part 151c, and a control substrate 151g for controlling the liquid level detection sensor 151e and the pressure detection sensor 151f. The dispensing chips 50 and 60 are mounted by press fitting the front end part 151h of the nozzle part 151a to the opening 50a of the dispensing chip 50 and the opening 60a of the dispensing chip 60 (see FIG. 3).

The cap 151b made of resin is attached so as to be movable in the Z direction with respect to the nozzle part 151a. A rim part 151i contacted when the dispensing chips 50 and 60 are mounted is formed in the cap 151b made of resin.

The movement mechanism part 152 is configured by a motor 152a, a pulley 152b connected to the motor 152a, a pulley 152c arranged at a predetermined interval from the pulley 152b, a drive transmission belt 152d mounted to the pulley 152b and the pulley 152c, a ball screw 152d that rotates with the rotation of the pulley 152c and that is arranged so as to extend in the Z direction, a direct acting guide 152f arranged so as to extend in the Z direction, and a moving member 152g that moves with the rotation of the ball screw 152e and that is attached so as to be movable along the direct acting guide 152f, as shown in FIGS. 15 and 16. With this configuration, when the motor 152a is driven, the drive transmission belt 152d is driven by way of the pulley 152b, whereby the pulley 152c mounted with the drive transmission belt 152d rotates. Since the ball screw 152e is rotated with the rotation of the pulley 152c, the moving member 152g that moves with the rotation of the ball screw 152e moves along the Z direction along which the direct acting guide 152f extends.

The dismounting mechanism section 160 has a function of dismounting the crushing tool 30 (see FIG. 9) and the filtering tool 40 (see FIG. 12) held at the holding part 141, and the dispensing chips 50 and 60 (see FIG. 3) mounted to the suctioning and dispensing mechanism section 150. Furthermore, the dismounting mechanism section 160 also has a function of suppressing the tissue solution dripping from the used crushing tool 30 from attaching to the sample preparation container 10 and each section of the sample processing device 100, and suppressing the tissue solution and the filtrate dripping from the used dispensing chips 50 and 60 from attaching to the sample preparation container 10 and each section of the sample processing device 100. The dismounting mechanism section 160 includes a dismounting member 161 for dismounting the crushing tool 30 and the filtering tool 40 from the holding part 141, and a movement mechanism part 162 for moving the dismounting member 161 in the X direction, as shown in FIGS. 15, 16 and 23.

The dismounting member 161 includes a release nail 161a contacting the upper surface of the abutting part 141m of the holding part 141, a dispensing chip releasing hole 161b abutting against the rim part 151i of the cap 151b of the suctioning and dispensing mechanism section 150, and a receiving part 161c made of resin for receiving the tissue solution and the filtrate.

The movement mechanism part 162 is configured by a motor 162a, a pulley 162b connected to the motor 162a, a pulley 162c arranged at a predetermined interval from the pulley 162b, a drive transmission belt 162d mounted to the pulley 162b and the pulley 162c, a direct acting guide 162e arranged so as to extend in the X direction, and a moving member 162f attached so as to be movable along the direct acting guide 162e. With this configuration, when the motor 162a is driven, the drive transmission belt 162d is driven by way of the pulley 162b, whereby the moving member 162f coupled to the drive transmission belt 162d moves in the X direction. The dismounting member 161 attached to the moving member 162f thus moves in the X direction.

The controlling section 170 is arranged to control each section of the sample processing device 100, as shown in FIGS. 15 and 16. Specifically, the controlling section 170 is electrically connected to the motors 132a, 142a, 152a, and 162a of each movement mechanism part 132, 142, 152, and 162, and has a function of transmitting the control signal for controlling the drive of each motor 132a, 142a, 152a and 162a. The movement of the installation part 131, the holding part 141, the syringe part 151 and the dismounting member 161 is thus controlled. The controlling section 170 is electrically connected to the fans 1311 and the Peltier element (not shown) of the temperature controlling part 131c of the installation part 131, and has a function of transmitting the control signal for controlling the rotation of the fan 1311 and the Peltier element. Thus, the tissue solution stored in the sample preparation kit 1 and the filtrate accommodated in the collection container 300 can be controlled to a predetermined temperature.

FIGS. 25 to 50 are views for explaining the operation of obtaining the filtrate of the sample processing device employing the sample preparation kit according to one embodiment of the present invention. The obtaining operation of the filtrate of the sample processing device 100 will now be described with reference to FIGS. 3, 12, 14 to 16, and 19 to 50.

The lid 20 (see FIG. 3) and the film 90 (see FIG. 3) are dismounted from the sample preparation container 10 (see FIG. 3), and the sample preparation kit 1 with the lymph node 200 cut in advance accommodated in the crushing process accommodating chamber 13. The prepared sample preparation kit 1 is installed in the installation part 131 discharged to the outside by pushing the eject button 180 of the sample processing device 100. As shown in FIG. 25, the installation part 131 is moved in the X1 direction by driving the motor 132a (see FIGS. 15 and 16) of the movement mechanism part 132 so that the position in the horizontal direction (X direction) of the mounting part 141a of the holding part 141 and the position in the horizontal direction of the crushing tool accommodating chamber 12 accommodating the crushing tool 30 to be matched therein. When the motor 142a (see FIGS. 15 and 16) of the movement mechanism part 142 is driven in such state, the holding part 141 moves in the Z1 direction (downward). The notch 32f of the outer side crushing member 32 engages with the projection 141j of the mounting part 141a, and the engagement nail 32g engages with the groove 141k of the mounting part 141a, so that the crushing tool 30 is press fitted mounted to the mounting part 141a, as shown in FIG. 20. Thereafter, the state shown in FIG. 26 is obtained by moving the holding part 141 in the Z2 direction (upward).

As shown in FIG. 27, the installation part 131 is moved in the X1 direction so that the position in the horizontal direction (X direction) of the mounting part 141a mounted with the crushing tool 30 and the position in the horizontal direction of the crushing process accommodating chamber 13 accommodating the lymph node 200 and the crushing solution 70 to be matched with each other. The lymph node 200 is crushed in the crushing process accommodating chamber 13 by moving the holding part 141 in the Z1 direction (downward). Specifically, the lymph node 200 is crushed to a predetermined size by repeatedly moving the crushing tool 30 in the Z1 direction (downward) and the Z2 direction (upward), as shown in FIG. 28. Thereafter, the inner side crushing member 31 is rotated in the crushing solution 70 with the lymph node 200 of a predetermined size floating therein by driving the motor (see FIG. 19) of the holding part 141, as shown in FIG. 29. The lymph node 200 is thus further fined and homogenized tissue solution is obtained in the crushing solution 70, as shown in FIG. 30.

As shown in FIG. 31, the crushing tool 30 is pulled up from the tissue solution by moving the mounting part 141a attached with the crushing tool 30 in the Z2 direction (upward). The dismounting member 161 is moved in the X2 direction up to the position below the crushing tool 30 that has been pulled up by moving the motor 162a (see FIGS. 15, 16, and 23) of the movement mechanism part 162. Even if the tissue solution dropped from the crushing tool 30 pulled up from the tissue solution, the tissue solution is received by the receiving part 161c (see FIGS. 23 and 24) of the dismounting member 161.

As shown in FIG. 32, the installation part 131 is moved in the X2 direction and the dismounting member 161 is moved in the X1 direction so that the position in the horizontal direction (X direction) of the mounting part 141a mounted with the crushing tool 30 and the position in the horizontal direction of the crushing tool accommodating chamber 12 to be matched with each other. Thereafter, the holding part 141 is moved in the Z1 direction (downward) to accommodate the crushing tool 30 in the crushing tool accommodating chamber 12, as shown in FIG. 33. Specifically, the holding part 141 is moved in the Z1 direction (downward), and the dismounting member 161 is moved in the X2 direction so that the release nail 161a of the dismounting member 161 is positioned on the upper part of the abutting part 141m of the holding part 141 that has moved, as shown in FIG. 33. Furthermore, by moving the holding part 141 in the Z2 direction (upward) in this state, and the collar part 32d of the crushing tool 30 is pressed against the lower part of the abutting part 141m, whereby force is applied to the collar part 32d of the outer side crushing member 32 from the abutting part 141m in the Z1 direction (downward) (direction of dismounting the crushing tool 30 from the mounting part 141a), and the outer side crushing member 32 (crushing tool 30) is separated from the mounting part 141a.

As shown in FIG. 34, the installation part 131 is moved in the X1 direction so that the position in the horizontal direction (X direction) of the nozzle part 151a of the syringe part 151 and the position in the horizontal direction of the dispensing chip accommodating part 15c of the dispensing chip accommodating chamber 15 accommodating the dispensing chip 50 to be matched with each other. The syringe part 151 is moved in the Z1 direction (downward) by driving the motor 152a (see FIGS. 15 and 16) of the movement mechanism part 152 in this state. As shown in FIG. 22, the dispensing chip 50 is mounted to the nozzle part 151a as the opening 50a of the dispensing chip 50 is press fitted to the front end part 151h of the nozzle part 151a. The state shown in FIG. 35 is obtained by moving the syringe part 151 in the Z2 direction (upward).

As shown in FIG. 36, the installation part 131 is moved in the X1 direction so that the position in the horizontal direction (X direction) of the nozzle part 151a mounted with the dispensing chip 50 and the position in the horizontal direction of the crushing process accommodating chamber 13 accommodating the tissue solution to be matched with each other. As shown in FIG. 37, the syringe part 151 is moved in the Z1 direction (downward), and the tissue solution in the crushing process accommodating chamber 13 is suctioned. Specifically, the contact of the front end part 50b of the dispensing chip 50 to the liquid level of the tissue solution is detected by the liquid level detection sensor 151e (see FIG. 21), and the tissue solution is suctioned by the pump part 151c (see FIG. 21) using the driving force of the motor 151d (see FIG. 21). Subsequently, the dispensing chip 50 is pulled up from the tissue solution by moving the nozzle part 151a mounted with the dispensing chip 50 in the Z2 direction (upward). The dismounting member 161 is moved in the X2 direction to the position below the dispensing chip 50 that has been pulled up. Thereafter, the installation part 131 is moved in the X1 direction and then the dismounting member 161 is moved in the X1 direction so that the position in the horizontal direction (X direction) of the nozzle part 151a mounted with the dispensing chip 50 and the position in the horizontal direction of the filter process accommodating chamber 14 to be matched with each other.

As shown in FIG. 38, the syringe part 151 is moved in the Z1 direction (downward), and the tissue solution suctioned at the crushing process accommodating chamber 13 is discharged and stirred in the filter process accommodating chamber 14. Specifically, the contact of the front end part 50b of the dispensing chip 50 with the liquid level of the diluted solution is detected by the liquid level detection sensor 151e (see FIG. 21), and the tissue solution is discharged by the pump part 151c (see FIG. 21) using the driving force of the motor 151d. The tissue solution is stirred by repeatedly performing suction and discharge in the diluted solution discharged with the tissue solution using the pump part 151c.

The dispensing chip 50 is pulled up from the diluted tissue solution by moving the nozzle part 151a mounted with the dispensing chip 50 in the Z2 direction (upward). The dismounting member 161 is moved in the X2 direction up to the position below the dispensing chip 50 that has been pulled up. The installation part 131 is moved in the X1 direction and the dismounting member 161 is moved in the X1 direction so that the position in the horizontal direction (X direction) of the nozzle part 151a mounted with the dispensing chip 50 and the position in the horizontal direction of the dispensing chip accommodating part 15c of the dispensing chip accommodating chamber 15 to be matched with each other.

Subsequently, the dispensing chip 50 is accommodated in the dispensing chip accommodating part 15c by moving the syringe part 151 in the Z1 direction (downward), as shown in FIG. 39. Specifically, the syringe part 151 is moved in the Z1 direction (downward), and the dismounting member 161 is moved in the X2 direction so that the dispensing chip releasing hole 161b (see FIG. 24) of the dismounting member 161 is positioned on the upper part of the rime part 151i of the cap 151b of the syringe part 151 that has been moved. The dispensing chip 50 is pressed against the lower part of the rim part 151i of the cap 151b by moving the syringe part 151 in the Z2 direction (upward) in this state, whereby force is applied to the dispensing chip 50 from the cap 151b in the Z1 direction (downward) (direction of dismounting the dispensing chip 50 from the nozzle part 151a), and the dispensing chip 50 is separated from the nozzle part 151a.

As shown in FIG. 40, the installation part 131 is moved in the X1 direction and then the holding part 141 is moved in the Z1 direction (downward) so that the position in the horizontal direction (X direction) of the mounting part 141a of the holding part 141 and the position in the horizontal position of the filtering tool accommodating chamber 11 accommodating the filtering tool 40 to be matched with each other. The notch 40f (see FIG. 14) of the filtering tool 40 then engages with the projection 141j of the mounting part 141a, and the engagement nail 40g (see FIGS. 12 and 14) engages with the groove 141k (see FIG. 20) of the mounting part 141a, so that the filtering tool 40 is press fitted mounted to the mounting part 141a. The state shown in FIG. 41 is then obtained by moving the holding part 141 in the Z2 direction (upward).

As shown in FIG. 42, the installation part 131 is moved in the X1 direction so that the position in the horizontal direction (X direction) of the mounting part 141a mounted with the filtering tool 40 and the position in the horizontal direction of the filter process accommodating chamber 14 accommodating the diluted tissue solution to be matched with each other. The diluted tissue solution is filtered in the filter process accommodating chamber 14 by moving the holding part 141 in the Z1 direction (downward). Specifically, the holding part 141 is first moved in the Z1 direction (downward) to insert the filtering tool 40 into the filter process accommodating chamber 14, as shown in FIG. 43. Since the opening cross sectional area of the filter process accommodating chamber 14 is formed so as to gradually reduce from the opening 14a side towards the bottom surface part 14b side, the diluted tissue solution is suppressed from leaking from the gap between the side surface of the filtering tool 40 and the filter process accommodating chamber 14. As shown in FIG. 44, the diluted tissue solution stored between the filtering tool 40 and the filter processing accommodating chamber 14 passes through two filters 41 and 42, and then extracted to the inside of the filtering tool 40 of cylindrical body.

As shown in FIG. 45, the dismounting member 161 is moved in the X2 direction so that the release nail 161a of dismounting member 161 is positioned on the upper part of the abutting part 141m (see FIG. 19) of the holding part 141. Furthermore, the collar part 40d (see FIG. 12) of the filtering tool 40 is pressed against the lower part of the abutting part 141m by moving the holding part 141 in the Z2 direction (upward) in this state, whereby force is applied to the collar part 40d of the filtering tool 40 from the abutting part 141m in the Z1 direction (downward) (direction of dismounting the filtering tool 40 from the mounting part 141a), the filtering tool 40 is separated from the mounting part 141a and the filtering tool 40 is fitted into the filter process accommodating chamber 14.

The installation part 131 is moved in the X2 direction and the syringe part 151 is moved in the Z1 direction (downward) so that the position in the horizontal direction (X direction) of the nozzle part 151a of the syringe part 151 and the position in the horizontal direction of the dispensing chip accommodating part 15d accommodating the dispensing chip 60 to be matched with each other. The opening 60a (see FIG. 3) of the dispensing chip 60 is press fitted into the front end part 151h (see FIG. 22) of the nozzle part 151a, and the dispensing chip 60 is mounted to the nozzle part 151a. Thereafter, the syringe part 151 is moved in the Z2 direction (upward) and the installation part 131 is moved in the X2 direction, so that the position in the horizontal direction (X direction) of the nozzle part 151a mounted with the dispensing chip 60 and the position in the horizontal direction of the filter process accommodating chamber 14 accommodating the filtrate match to obtain the state shown in FIG. 46.

After the syringe part 151 is moved in the Z1 direction (downward), the filtrate in the filter process accommodating chamber 14 is suctioned, as shown in FIG. 47. Subsequently, the dispensing chip 60 is pulled up from the filtrate by moving the nozzle part 151a mounted with the dispensing chip 60 in the Z2 direction (upward). The dismounting member 161 is moved in the X2 direction up to the position below the dispensing chip 60 that has been pulled up. As shown in FIG. 48, the installation part 131 is then moved in the X1 direction and then the dismounting member 161 is moved in the X1 direction so that the position in the horizontal direction (X direction) of the nozzle part 151a mounted with the dispensing chip 60 and the position in the horizontal direction of the collection container 300 installed in the collection container installation part 131b of the installation part 131 to be matched with each other.

As shown in FIG. 49, the syringe part 151 is then moved in the Z1 direction (downward), and the filtrate suctioned in the filter process accommodating chamber 14 is discharged to the collection container 300. Consequently, the filtrate obtained form the lymph node 200 can be obtained in the collection container 300.

The nozzle part 151a mounted with the dispensing chip 60 is moved in the Z2 direction (upward), and the dismounting member 161 is moved in the X2 direction up to the position below the dispensing chip 60 that has been pulled up. The installation part 131 is moved in the X2 direction and the dismounting member 161 is moved in the X1 direction so that the position in the horizontal direction (X direction) of the nozzle part 151a mounted with the dispensing chip 60 and the position in the horizontal direction of the dispensing chip accommodating part 15d of the dispensing chip accommodating chamber 15 to be matched with each other.

As shown in FIG. 50, the dispensing chip 50 is accommodated in the dispensing chip accommodating part 15c by moving the syringe part 151 in the Z1 direction (downward) Thereafter, the dispensing chip 60 is separated from the nozzle part 151a through procedures similar to the separation of the dispensing chip 50.

The obtaining operation of the filtrate of the sample processing device 100 is thus performed in the above manner.

In the present embodiment, since the crushing tool 30 received from the opening 13a easily reaches (abuts) the convex part 13c of the inner bottom surface of the bottom surface part 13b by forming a convex part 13c of semicircular shape corresponding to the concave part 31a of semicircular shape of the inner side crushing member 31 of the crushing tool 30 on the inner bottom surface of the bottom surface part 13b of the crushing process accommodating chamber 13, as described above, generation of the portion (dead space) where the crushing tool 30 received from the opening 13a does not reach the convex part 13c of the bottom surface part 13b of the crushing process accommodating chamber 13 is suppressed. As a result, the possibility of the lymph node 200 entering into the portion not reached by the crushing tool 30 does not occur, and thus the lymph node 200 is reliably crushed using the crushing tool 30 received from the opening 13a.

Furthermore, in the present embodiment, the lymph node 200 can be further fined since the small lymph node 200 crushed to a certain extent can be sandwiched between the concave part 31a of the inner side crushing member 31 and the convex part 13c of the crushing process accommodating chamber 13 by forming the surface of the convex part 13c of the bottom surface part 13b of the crushing process accommodating chamber 13 and the surface of the concave part 31a of the inner side crushing member 31 to substantially the same curvature radius.

In the present embodiment, the convex part 13c having a rib shape of cross form is formed on the inner bottom surface of the bottom surface part 13b of the crushing process accommodating chamber 13, and the gap 13d is formed between the concave part 31a of the flat plate shaped front end part of the inner side crushing member 31 and the portion other than the convex part 13c of the crushing process accommodating chamber 13 when the concave part 31a of the flat plate shaped front end part of the inner side crushing member 31 is rotated with respect to the convex part 13c of rib shape of cross form, and thus the lymph node 200 that has entered the gap 13d can be taken in with the rotation of the inner side crushing member 31 when the inner side crushing member 31 is rotated with respect to the convex part 13c with the lymph node 200 entered in the gap 13d between the concave part 31a of the inner side crushing member 31 and the portion other than the convex part 13c of the crushing process accommodating chamber 13. As a result, the lymph node 200 which has been taken in is sandwiched between the concave part 31a of the inner side crushing member 31 and the convex part 13c of the crushing process accommodating chamber 13, and thus the lymph node 200 is more reliably crushed.

In the present embodiment, the outer peripheral surface of the filtering tool 40 and the inner peripheral surface of the filter process accommodating chamber 14 contact thereby suppressing the tissue solution from leaking upward from the side surface of the filtering tool 40 when the filtering tool 40 is inserted from the opening 14a side towards the bottom surface part 14b side and has reached a predetermined inserting amount by forming the filter process accommodating chamber 14 from the opening 14a side towards the bottom surface part 14b side so that the opening cross sectional area gradually decreases, and thus the filtrate is extracted through the two films 41 and 42 attached to the filter installation part 40a of the filtering tool 40. The tissue solution between the filtering tool 40 and the bottom surface part 14b of the filter process accommodating chamber 14 can be readily extracted through the filters 41 and 42 of the filtering tool 40, and the filtrate can be readily extracted from the tissue solution obtained by crushing the lymph node 200.

In the present embodiment, the crushing tool 30 is configured by the inner side crushing member 31 having a concave part 31 formed so as to correspond to the convex part 13c of the crushing process accommodating chamber 13 of the sample preparation container 10, and the outer side crushing member 32 made of a cylindrical body that can accommodate the inner side crushing member 31 therein. The inner side crushing member 31 is configured to be relatively rotatable with respect to the outer side crushing member 32, and thus the lymph node 200 that has entered between the inner side crushing member 31 and the outer side crushing member 32 is easily crushed since the inner side crushing member 31 relatively rotates with respect to the outer side crushing member 32. Consequently, the lymph node 200 is reliably and rapidly crushed since the lymph node 200 is crushed by both between the concave part 31a of the inner side crushing member 31 and the convex part 13c of the crushing process accommodating chamber 13, and between the inner side crushing member 31 and the outer side crushing member 32.

In the present embodiment, by forming a plurality of slits 32c in the outer side crushing member 32, the lymph node 200 crushed between the concave part 31a of the inner side crushing member 31 and the convex part 13c of the crushing process accommodating chamber 13, and between the inner side crushing member 31 and the outer side crushing member 32 flows towards the outer side of the outer side crushing member 32 through the plurality of slits 32c from between the inner side crushing member 32 and the outer side crushing member 32. Thus, the lymph node 200 is suppressed from retaining between the inner side crushing member 31 and the outer side crushing member 32. As a result, the lymph node 200 can be circulated between the inner side and the outer side of the outer side crushing member 32 made of a cylindrical body, and thus the circulating lymph node 200 is more reliably crushed by the inner side crushing member 31 and the outer side crushing member 32.

In the present embodiment, the filtering tool 40 of cylindrical shape having the opening 40e formed on the upper part side and filters 41 and 42 arranged on the lower part side is held by the holding member 141 of the sample process mechanism section 140, and the held filtering tool 40 is moved using the movement mechanism part 142, so that the tissue solution stored in the filter process accommodating chamber 14 is filtered by means of the filtering tool 40 having the opening 40e on the upper part side by inserting the filtering tool 40 into the filter process accommodating chamber 14 of the sample preparation container 10 accommodating the tissue solution obtained by crushing the lymph node. In this case, by configuring so that the filtrate is extracted to the inside of the filtering tool 40, the dispensing chip 60 can be inserted inside the filtering tool 60 through the opening 40e on the upper part side of the filtering tool 40, and thus the filtrate can be suctioned by the dispensing chip 60. As a result, the filtrate extracted by filtering the tissue solution obtained by crushing the lymph node can be collected.

In the present embodiment, the suctioning and dispensing mechanism section 150 mounted with the dispensing chip 60 for suctioning and dispensing the filtrate is arranged, as described above, so that the extracted filtrate is suctioned through the opening 40e of the filtering tool 40 and the suctioned filtrate is dispensed to the collection container 300 by the suctioning and dispensing mechanism section 150 (dispensing chip 60). The filtrate can be thus easily collected by the suctioning and dispensing mechanism section 150 (dispensing chip 60).

Furthermore, in the present embodiment, the suctioning and dispensing mechanism section 150 is configured so as to be mounted with the dispensing chip 50 for suctioning the tissue solution prepared in the crushing process accommodating chamber 13 of the sample preparation container 10 and dispensing the suctioned tissue solution to the filter process accommodating chamber 14 of the sample preparation container 10, whereby a mechanism section for conveying the tissue solution prepared in the crushing process accommodating chamber 13 to the filter process accommodating chamber 14 does not need to be separately arranged, and thus the number of components is reduced and the device is miniaturized.

In the present embodiment, the holding member 141 of the sample process mechanism section 140 is configured so as to hold the crushing tool 30 for crushing the lymph node, so that the crushing tool 30 is held by the holding member 141 when crushing the lymph node and preparing the tissue solution, and the filtering tool 40 is held by the holding member 141 when filtering the tissue solution, and thus preparation and filtration of the tissue solution are performed in one device. When performing preparation and filtration of the tissue solution in one device, the mechanism section for holding the crushing tool 30 and inserting the crushing tool 30 into the crushing process accommodating chamber 13 does not need to be separately arranged, and thus the number of components is reduced and the device is miniaturized.

In the present embodiment, the holding member 141 is configured so as to be movable in the up and down direction by the movement mechanism part 142, and thus when the holding member 141 is moved in the downward direction by the movement mechanism part 142 when the holding member 141 is arranged above the sample preparation container 10, the lymph node is easily crushed and the tissue solution is easily prepared, and further, filtration of the tissue solution can be performed.

In the present embodiment, by arranging the press-fit part 141i to where the filtering tool 40 and the crushing tool 30 are press fitted in the holding member 141 of the sample processing mechanism section 140, the filtering tool 40 and the crushing tool 30 are easily held by the holding member 141 by press fitting the filtering tool 40 and the crushing tool 30 to the press-fit part 141i. In this case, if the filtering tool 40 and the crushing tool 30 before use are accommodated in the sample preparation container 10, the filtering tool 40 and the crushing tool 30 before use that are accommodated in the sample preparation container 10 may easily be press fitted and held at the press-fit part 141i of the holding member 141 by moving the holding member 141 downward by the movement mechanism part 142.

Furthermore, in the present embodiment, by arranging the dismounting mechanism section 160 for dismounting at least one of either the filtering tool 40 or the crushing tool 30 held at the holding member 141 of the sample process mechanism section 140 from the holding member 141, as described above, the crushing tool 30 is dismounted from the holding member 141 by the dismounting mechanism section 160 and the filtering tool 40 may be mounted when moving from the preparation step of the tissue solution to the filtration step of the tissue solution, and the filtering tool 40 is dismounted from the holding member 14 by the dismounting mechanism section 160 and the crushing tool 30 may be mounted when moving from the filtration step of the tissue solution to the preparation step of the tissue solution.

In the present embodiment, by having at least the filtering tool 40 or the crushing tool 30 dismountable from the holding member 141 by moving the holding member 141 upward by the movement mechanism part 142 with the dismounting member 161 moved in the horizontal direction by the movement mechanism part 162 and arranged at the dismounting position, even if the holding member 141 for holding the filtering tool 40 and the crushing tool 30 is configured to be movable only in the up and down direction, at least the filtering tool 40 or the crushing tool 30 can be easily dismounted from the holding member 141 by the movement of the holding member 141 in the up and down direction and the movement of the dismounting member 161 in the horizontal direction.

In the present embodiment, the installation part 131 for installing the sample preparation container 10 and the movement mechanism part 132 for moving the installation part 131 in the horizontal direction are arranged, as described above, so that the positions in the horizontal direction of the holding member 141 holding the filtering tool 40 and the filter process accommodating chamber 14 of the sample preparation container 10 match when filtering the tissue solution, and the positions in the horizontal direction of the holding member 141 holding the crushing tool 30 and the crushing process accommodating chamber 13 of the sample preparation container 10 match when preparing the tissue solution even if the holding member 141 is configured to be movable only in the up and down direction by moving the installation part 131 mounted with the sample preparation container 10 in the horizontal direction by means of the movement mechanism part 132. Therefore, even if the holding member 14 is configured to be movable only in the up and down direction, the filtering tool 40 can be inserted to the filter process accommodating chamber 14 of the sample preparation container 10 when filtering the tissue solution, and the crushing tool 30 can be inserted into the crushing process accommodating chamber 13 of the sample preparation container 10 when preparing the tissue solution.

The embodiment disclosed herein is merely illustrative and should not be construed as limiting in all aspects. The scope of the present invention is not defined by the description of the embodiments but is defined by the appended claims and encompasses the definitions equivalent to the scope of the claims and all modifications within the scope.

For example, in the above embodiment, an example in which the convex part of semicircular shape when seen from the front is arranged at the inner bottom surface of the bottom surface part of the crushing solution storing chamber is described, but the present invention is not limited thereto, and the convex part having a shape other than the semicircular shape may be arranged. The convex shape of a square and the like may be arranged. In this case, the front end part of the inner side crushing member of the crushing tool must be formed into a concave part of square shape so as to correspond to the convex part of square shape.

In the above embodiment, an example in which the convex part is formed so as to have a rib shape of cross form when seen in a plane view, so that a gap is formed between the concave part of the inner side crushing member and the portion other than the convex part of the crushing solution storing chamber when the inner side crushing member is rotated is described, but the present invention is not limited thereto, and the gap does not need to be formed between the concave part of the inner side crushing member and the convex part of the crushing solution storing chamber.

In the above embodiment, an example in which the crushing tool for crushing the body tissue is configured by the inner side crushing member and the outer side crushing member is described, but the present invention is not limited thereto, and the body tissue may be crushed with one crushing member.

In the above embodiment, the lymph node is fined by inserting the crushing tool to the crushing process accommodating chamber accommodating the lymph node and the crushing solution from above, crushing the lymph node to a predetermined size by moving the crushing tool up and down, and then rotating the inner side crushing member of the crushing tool, but the present invention is not limited thereto, and the lymph node may be fined by inserting the crushing tool to the crushing process accommodating chamber accommodating the lymph node and the crushing solution from above, and rotating the inner side crushing member of the crushing tool while moving the crushing tool up and down.

In the present embodiment, only one collection container is installed, and the filtrate filtered in the filter process accommodating chamber is suctioned and then discharged into the one collection container by the dispensing chip, but the present invention is not limited thereto, and two collection containers may be installed, the diluted solution stored in the filter process accommodating chamber may be dispensed in advance into one of the collection containers by the dispensing chip, and the filtrate discharged to the other collection container may be suctioned and discharged to the former collection container by the dispensing chip to prepare the diluted sample.

For example, in the above embodiment, an example of applying the present invention to the sample processing device capable of performing preparation of the tissue solution and filtration of the tissue solution has been described, but the present invention is not limited thereto, and is also applicable to the sample processing device for performing only filtration of the tissue solution.

In the above embodiment, the holding member capable of holding both the crushing tool and the filtering tool is used, but the present invention is not limited thereto, and the holding member for holding the crushing tool, and the holding member for holding the filtering tool may be separately arranged.

In the above embodiment, collection of the filtrate, and conveyance of the tissue solution from the crushing process accommodating chamber to the filter process accommodating chamber are performed with one suctioning and dispensing mechanism section, but the present invention is not limited thereto, and the suctioning and dispensing mechanism section for collecting the filtrate, and the suctioning and dispensing mechanism section for conveying the tissue solution from the crushing process accommodating chamber to the filter process accommodating chamber may be separately arranged.

In the above embodiment, the lymph node is fined by inserting the crushing tool to the crushing process accommodating chamber accommodating the lymph node and the crushing solution from above, crushing the lymph node to a predetermined size by moving the crushing tool up and down, and then rotating the inner side crushing member of the crushing tool, but the present invention is not limited thereto, and the lymph node may be fined by inserting the crushing tool to the crushing process accommodating chamber accommodating the lymph node and the crushing solution from above, and rotating the inner side crushing member of the crushing tool while moving the crushing tool up and down.

In the above embodiment, only one collection container is installed, and the filtrate filtered in the filter process accommodating chamber is suctioned and then discharged into the one collection container by the dispensing chip, but the present invention is not limited thereto, and two collection containers may be installed, the diluted solution stored in the filter process accommodating chamber may be dispensed in advance into one of the collection containers by the dispensing chip, and the filtrate discharged to the other collection container may be suctioned and discharged to the former collection container by the dispensing chip to prepare the diluted sample.

It should be apparent to those skilled in the art that the present invention may be embodied in many other specific forms without departing from the spirit or scope of the invention. Therefore, the present invention is not to be limited to the details given herein, but may be modified within the scope and equivalence of the appended claims.

What is claimed is:

1. A sample preparation kit, comprising:
    a container for containing tissue isolated from a living body and comprising a convex part on an inner bottom of the container, wherein the convex part comprises a first convex part having a semicircular plate shape and a second convex part having a semicircular plate shape which cross each other; and
    a crushing tool comprising a flat plate having a concave part for crushing the tissue contained in the container between the convex part and the concave part, wherein the concave part has a curved shape corresponding to the semicircular plate shape of each of the first and the second convex parts, wherein a gap is formed between the concave part and the inner bottom of the container when the concave part is rotated with respect to the convex part.

2. The sample preparation kit according to claim 1, further comprising
    a crushing tool holder for holding the crushing tool.

3. The sample preparation kit according to claim 2, wherein the container for containing tissue and the crushing tool holder are integrally formed.

4. The sample preparation kit according to claim 2, further comprising
    a solution comprising a nonionic surface active agent, for forming tissue homogenate in the container,
    wherein the tissue is crushed in the solution.

5. The sample preparation kit according to claim 4, further comprising
    a container for filtering a tissue solution obtained by crushing the tissue in the solution, and
    a diluent for diluting the tissue solution,
    wherein the diluent is contained in the container for filtering a tissue solution.

6. The sample preparation kit according to claim 5, further comprising
    a filtering tool for filtering the tissue solution in the container for filtering a tissue solution,
    a filtering tool holder for holding the filtering tool,
    wherein the filtering tool is held in the filtering tool holder.

7. The sample preparation kit according to claim 6, further comprising
    a dispensing tool for dispensing the tissue solution to the container for filtering a tissue solution,
    a dispensing tool holder for holding the filtering tool,
    wherein the dispensing tool holder is held in the dispensing tool holder.

8. The sample preparation kit according to claim 6, wherein the container for filtering a tissue solution and the filtering tool holder are integrally formed.

9. The sample preparation kit according to claim 1, wherein the flat plate of the crushing tool has the concave part at one end and crushes the tissue between the concave part and the convex part by rotating the crushing tool around an axis of the crushing tool.

10. The sample preparation kit according to claim 1, wherein the crushing tool includes an inner side crushing tool and an outer side crushing tool capable of accommodating the inner side crushing tool on the inside, the inner side crushing tool being rotatable relative to the outer side crushing tool and having the concave part.

11. The sample preparation kit according to claim 1, wherein the tissue is a lymph node.

12. A sample preparation kit, comprising:
    a container for containing tissue isolated from a living body and comprising a convex part on an inner bottom of the container, wherein the convex part comprises a first convex part having a semicircular plate shape and a second convex part having a semicircular plate shape;
    a solution comprising a nonionic surface active agent, for forming tissue homogenate in the container; and
    a crushing tool comprising a flat plate having a concave part for crushing the tissue in the solution between the convex part and the concave part, wherein the concave part has a curved shape corresponding to the semicircular plate shape of each of the first and the second convex parts wherein a gap is formed between the concave part and the inner bottom of the container when the concave part is rotated with respect to the convex part and,
    wherein the first convex part and the second convex part cross each other.

* * * * *